(12) United States Patent
Bloomfield

(10) Patent No.: US 12,178,846 B2
(45) Date of Patent: Dec. 31, 2024

(54) METHODS OF USING GAP JUNCTIONS AS THERAPEUTIC TARGETS FOR THE TREATMENT OF DEGENERATIVE DISORDERS OF THE RETINA

(71) Applicant: The Research Foundation for The State University of New York, Albany, NY (US)

(72) Inventor: Stewart Bloomfield, New York, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 15 days.

(21) Appl. No.: 15/687,719

(22) Filed: Aug. 28, 2017

(65) Prior Publication Data

US 2017/0354710 A1 Dec. 14, 2017

Related U.S. Application Data

(62) Division of application No. 15/317,171, filed as application No. PCT/US2015/035226 on Jun. 11, 2015, now abandoned.

(60) Provisional application No. 62/011,354, filed on Jun. 12, 2014.

(51) Int. Cl.

| | | |
|---|---|---|
| *A61K 47/44* | (2017.01) | |
| *A61K 9/00* | (2006.01) | |
| *A61K 31/19* | (2006.01) | |
| *A61K 31/196* | (2006.01) | |
| *A61K 31/7105* | (2006.01) | |
| *A61K 38/16* | (2006.01) | |
| *A61K 38/17* | (2006.01) | |
| *A61K 45/06* | (2006.01) | |
| *C12N 15/113* | (2010.01) | |

(52) U.S. Cl.
CPC .......... *A61K 38/177* (2013.01); *A61K 9/0019* (2013.01); *A61K 9/0048* (2013.01); *A61K 31/19* (2013.01); *A61K 31/196* (2013.01); *A61K 31/7105* (2013.01); *A61K 38/16* (2013.01); *A61K 45/06* (2013.01); *C12N 15/1138* (2013.01); *C12N 2310/11* (2013.01); *C12N 2320/31* (2013.01)

(58) Field of Classification Search
CPC ................ A61K 9/0048; A61K 9/0051; A61K 9/0019; A61K 31/382; A61K 31/00; A61K 49/00; A61K 31/436; A61K 47/12; A61L 2430/16; A61L 27/54; A61L 31/16; A61L 15/44; A61F 9/0017; A61F 2210/0004; A61F 2250/0067; A61P 27/02; A61P 17/02
See application file for complete search history.

(56) References Cited

U.S. PATENT DOCUMENTS

| | | | | |
|---|---|---|---|---|
| 5,474,985 A | * | 12/1995 | Polansky | A61K 31/19 424/468 |
| 6,369,116 B1 | * | 4/2002 | Wong | A61K 9/0024 424/486 |
| 6,379,882 B1 | * | 4/2002 | Bitler | C07D 233/64 435/4 |
| 2004/0167109 A1 | * | 8/2004 | Bingaman | A61K 31/573 514/176 |
| 2007/0066555 A1 | | 3/2007 | Becker et al. | |
| 2009/0142295 A1 | | 6/2009 | Becker et al. | |
| 2009/0220450 A1 | | 9/2009 | Green et al. | |
| 2009/0220516 A1 | * | 9/2009 | Laties | A61K 31/13 424/141.1 |
| 2010/0092469 A1 | * | 4/2010 | Simard | A61K 31/56 514/1.1 |
| 2012/0093768 A1 | | 4/2012 | Laux et al. | |
| 2013/0053425 A1 | * | 2/2013 | To | A61K 31/045 514/411 |
| 2013/0123334 A1 | | 5/2013 | Feinstein et al. | |
| 2017/0106047 A1 | | 4/2017 | Bloomfield | |

FOREIGN PATENT DOCUMENTS

WO 2014/040052 A2 3/2014

OTHER PUBLICATIONS

Paschon et al., Blocking of connexin-mediated communication promotes neuroprotection during acute degeneration induced by mechanical trauma, PLOS One, vol. 7, issue 9, e45449, pp. 1-12. (Year: 2012).*
Lambert et al., Neurotrophin and Trk expression by cells of the human lamina cribrosa following oxygen-glucose deprivation, BMC Neuroscience, vol. 5:51, pp. 1-15. (Year: 2004).*
Jung et al., The flavonoid bicalin counteracts ischemic and oxidative insults to retinal cells and lipid peroxidation to brain membranes, Neurochemistry, vol. 53, pp. 325-337. (Year: 2008).*
Niyadurupola et al., P2X7 receptor activation mediates retinal ganglion cell death in a human retina model of ischemic neurodegeneration, Investigative Ophthalmology & Visual Science, vol. 54, pp. 2163-2170. (Year: 2013).*
Hutnik et al., The protective effect of functional connexin 43 channels on a human epithelial cell line exposed to oxidative stress, IOVS, vol. 49, pp. 800-806. (Year: 2008).*
Stuart A. Lipton, Possible role for memantine in protecting retinal ganglion cells from glaucomatous damage, Survey of Ophthalmology, vol. 48, supplement 1, pp. S38-S46. (Year: 2003).*
Lambiase et al., Experimental and clinical evidence of neuroprotection by nerve growth factor eye drops: implications for glaucoma, PNAS, vol. 106, pp. 13469-13474. (Year: 2009).*

(Continued)

*Primary Examiner* — Dana H Shin
(74) *Attorney, Agent, or Firm* — Scully, Scott, Murphy & Presser, P.C.

(57) ABSTRACT

The disclosure provides methods of treating a condition of the retina by administering an inhibitor of connexin 36 and/or an inhibitor of connexin 45 to a subject with a retinal condition. This disclosure further provides compositions for the treatment of a retinal condition which include an inhibitor of connexin 36 and/or an inhibitor of connexin 45.

3 Claims, 15 Drawing Sheets
(15 of 15 Drawing Sheet(s) Filed in Color)
Specification includes a Sequence Listing.

(56) References Cited

OTHER PUBLICATIONS

Chen et al., Fenamates protect neurons against ischemic and excitotoxic injury in chick embryo retina, Neuroscience Letters, vol. 242, pp. 163-166. (Year: 1998).*

Kawakami et al., Isoliquiritigenin is a novel NMDA receptor antagonist in Kampo meidicine yokukansan, Cellular and Molecular Neurobiology, vol. 31, pp. 1203-1212. (Year: 2011).*

Pan et al., Screening of gap junction antagonists on dye coupling in the rabbit retina, Visual Neuroscience, vol. 24, pp. 609-618. (Year: 2007).*

Akopian A. et al. "Gap Junction-Mediated Death of Retinal Neurons is Connexin and Insult Specific: A Potential Target for Neuroprotection", The Journal of Neuroscience 34(32):10582-10591 (Aug. 6, 2014).

Blankenship A.G. et al., "The Role of Neuronal Connexins 36 and 45 in Shaping Spontaneous Firing Patterns in the Developing Retina", The Journal of Neuroscience 31(27):9998-10008 (Jul. 6, 2011).

Deans M.R. et al., "Connexin36 is Essential for Transmission of Rod-Mediated Visual Signals in the Mammalian Retina", Neuron 36:703-712 (Nov. 14, 2002).

Güldenagel M et al., "Visual Transmission Deficits in Mice With Targeted Disruption of the Gap Junction Gene Connexin36", The Journal of Neuroscience 21(16):6036-6044 (Aug. 15, 2001).

Kihara A H et al., "Expression of Connexins 36, 43 and 45 During Postnatal Development of the Mouse Retina", Journal of Neurobiology 66(13):1397-1410 (2006).

Maxeiner S. et al., "Deletion of Connexin45 in Mouse Retinal Neurons Disrupts the Rod/Cone Signaling Pathway Between AII Amacrine and ON Cone Bipolar Cells and Leads to Impaired Visual Transmission", The Journal of Neuroscience 25(3):566-576 (Jan. 19, 2005).

International Search Report dated Nov. 23, 2015 received in International Application No. PCT/US2015/035226.

Canadian Examination Report dated May 19, 2021 received in Canadian Application No. 2,951,721.

* cited by examiner

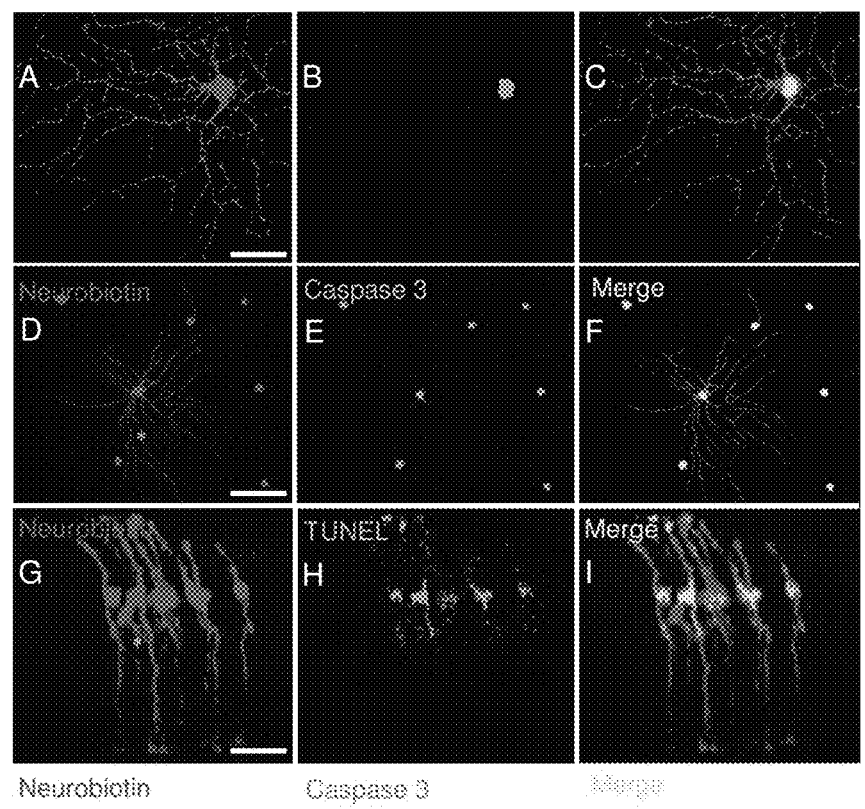
FIGS. 1A-I

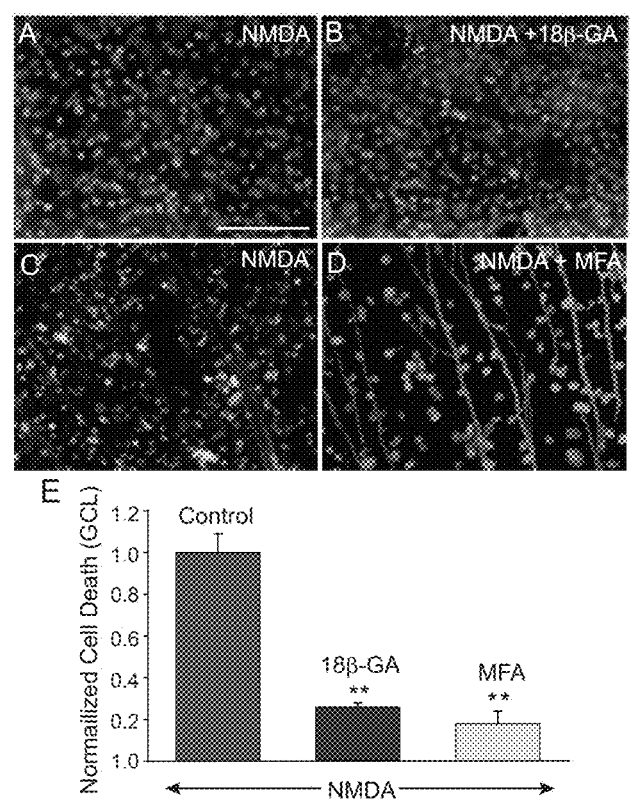
FIGS. 2A-E

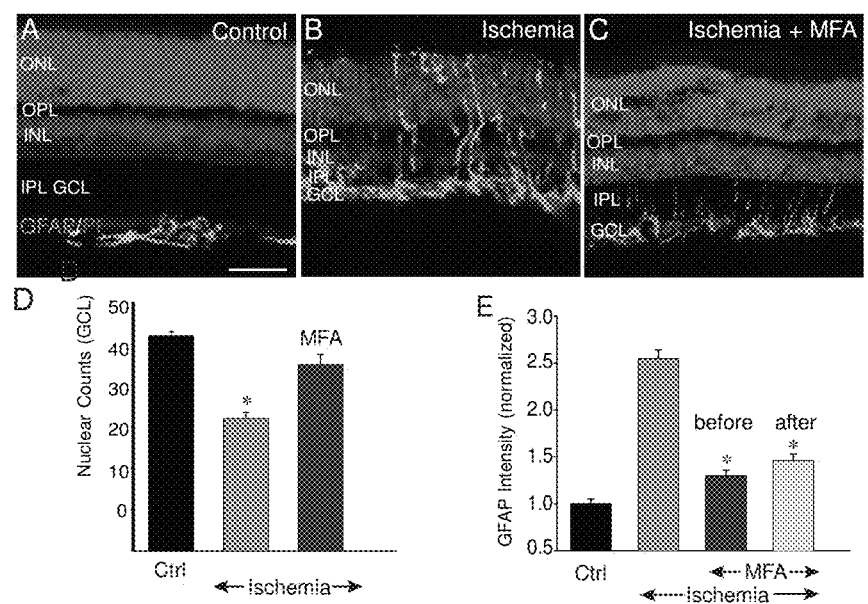
FIGS. 3A-E

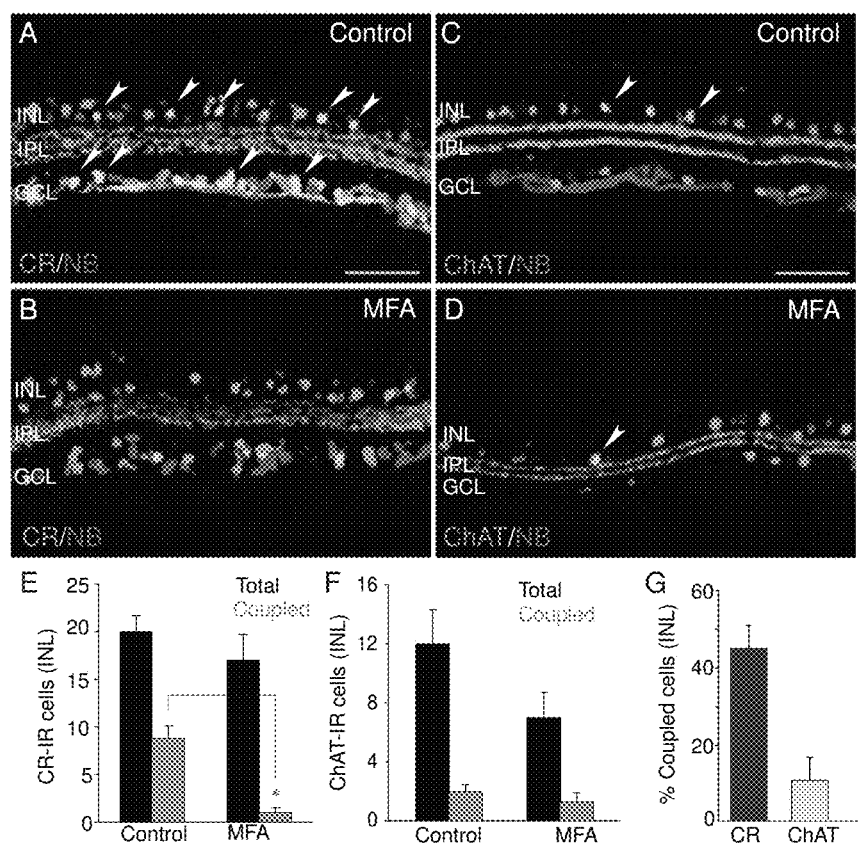
FIGS. 4A-G

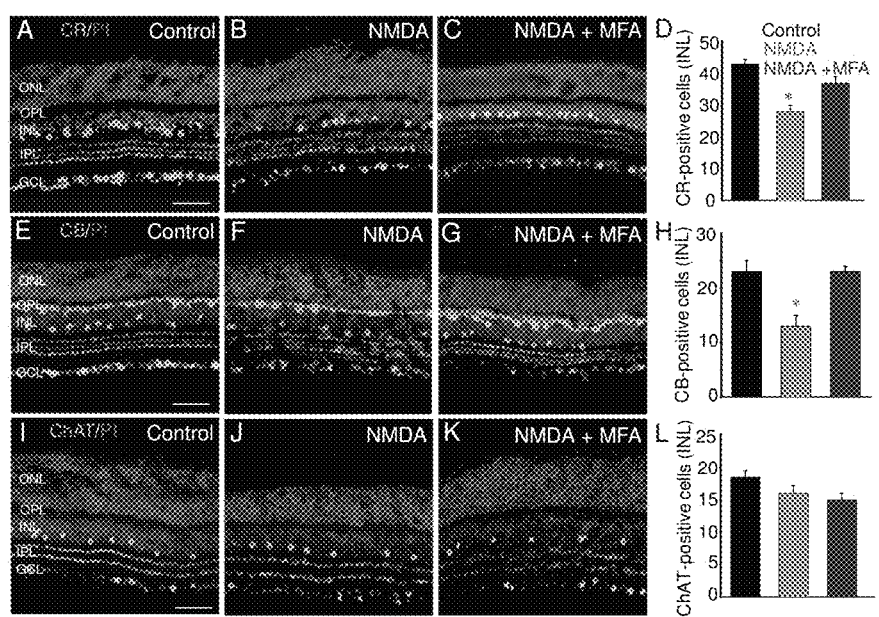
FIGS. 5A-L

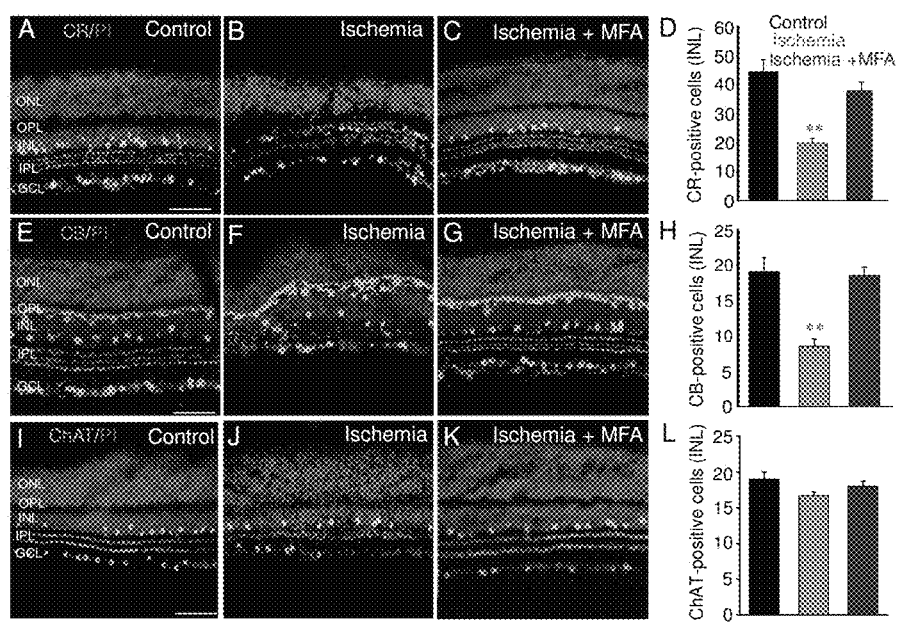
FIGS. 6A-L

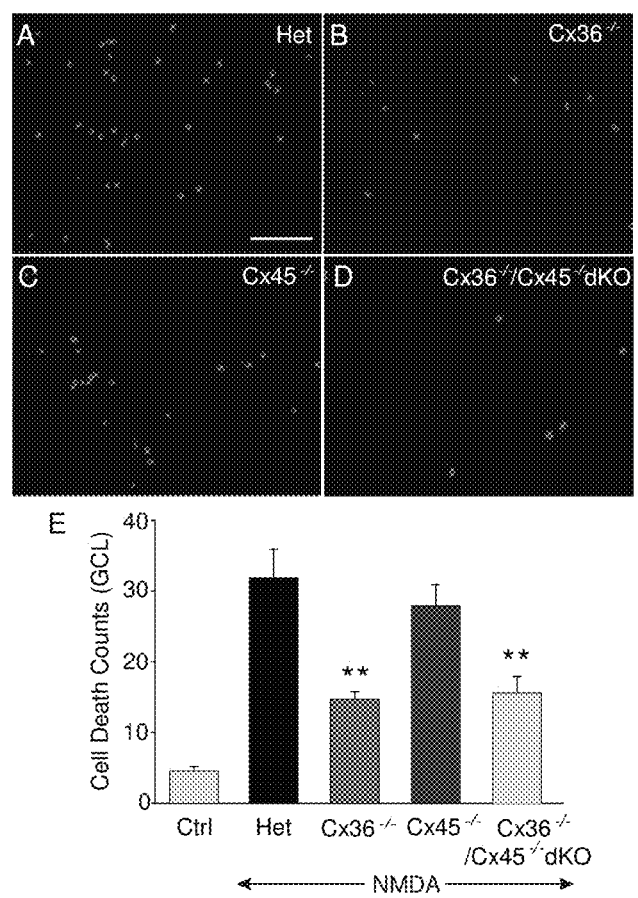
FIGS. 7A-E

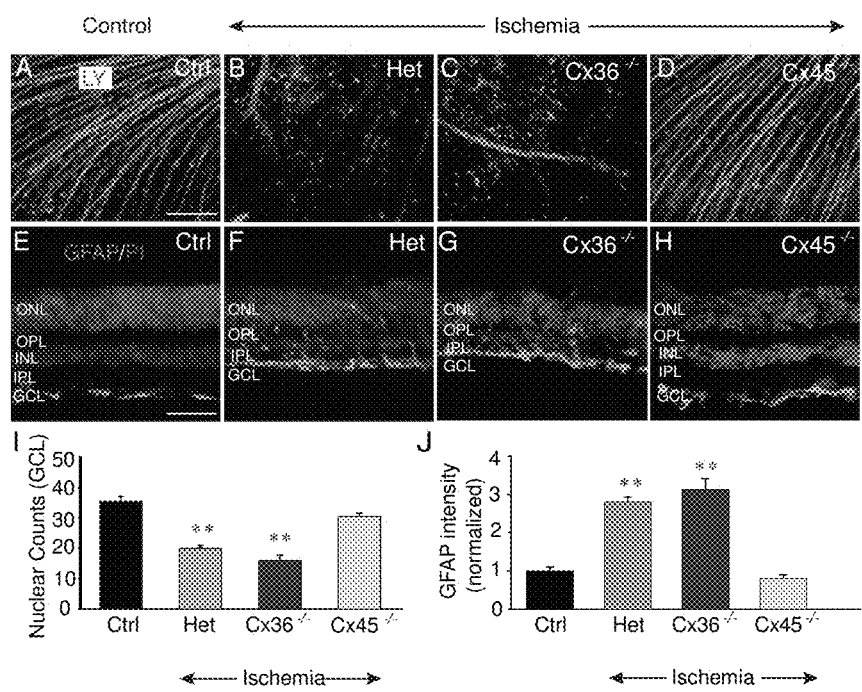
FIGS. 8A-J

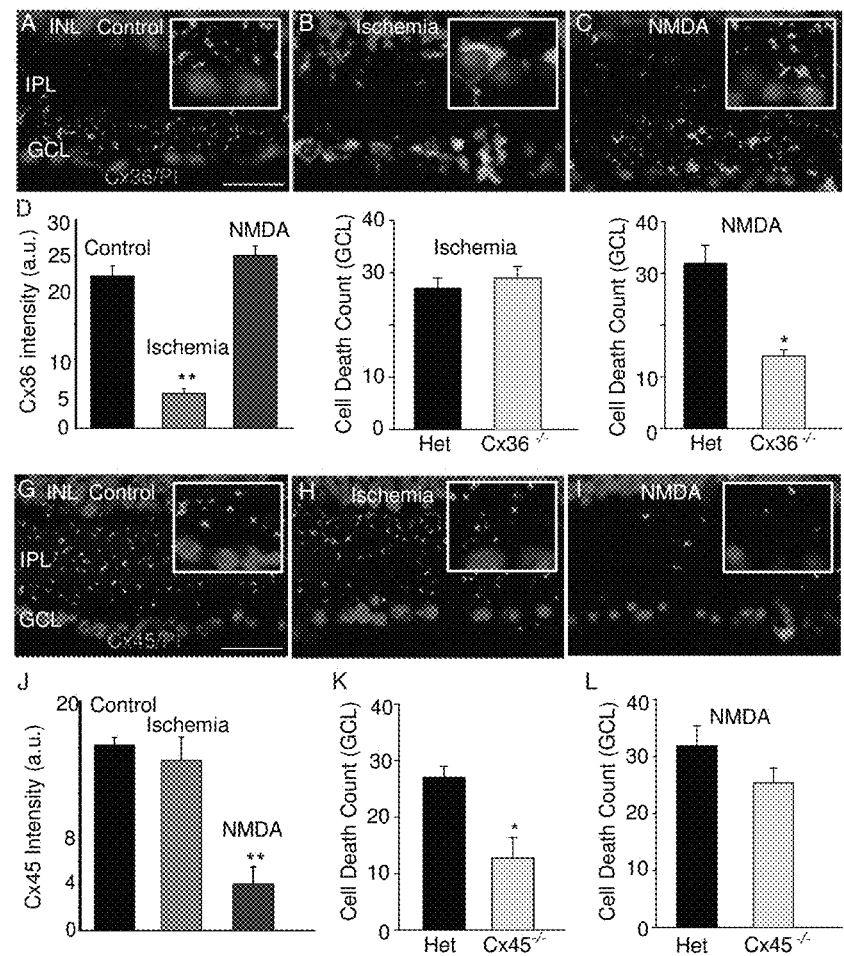
FIGS. 9A-L

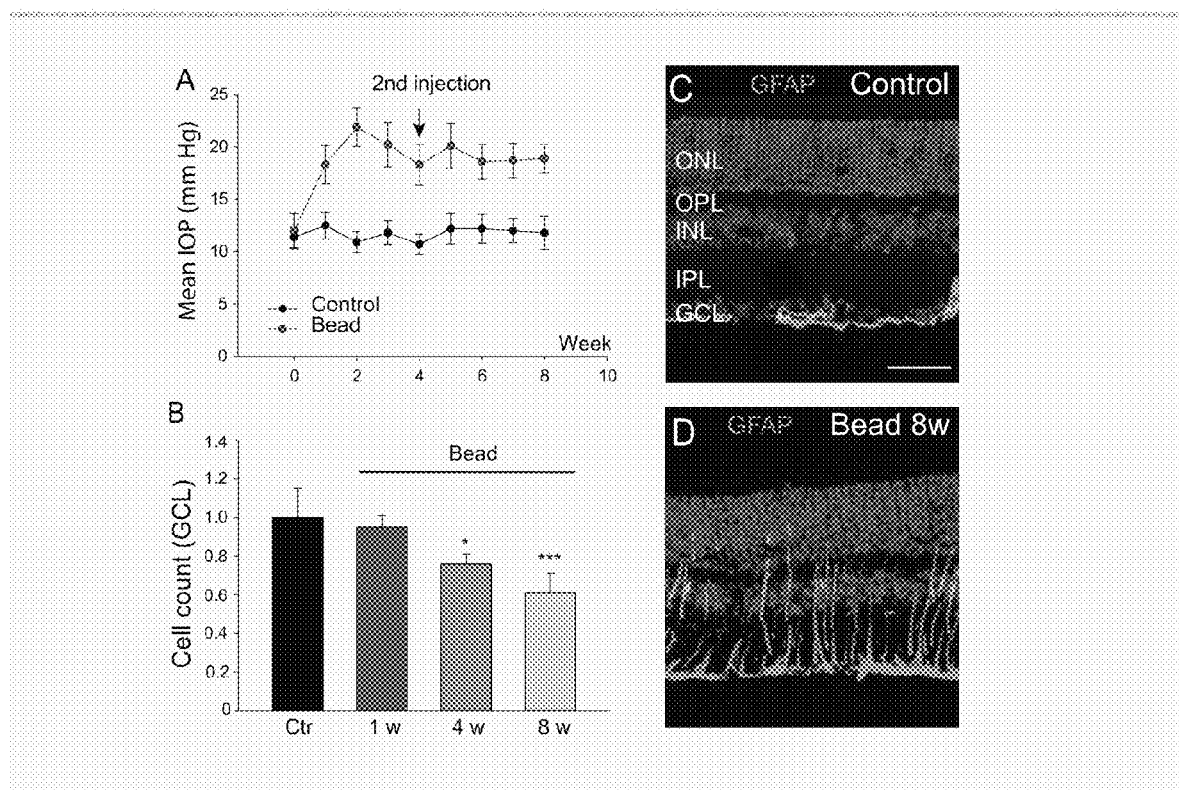
FIGS. 10A-D

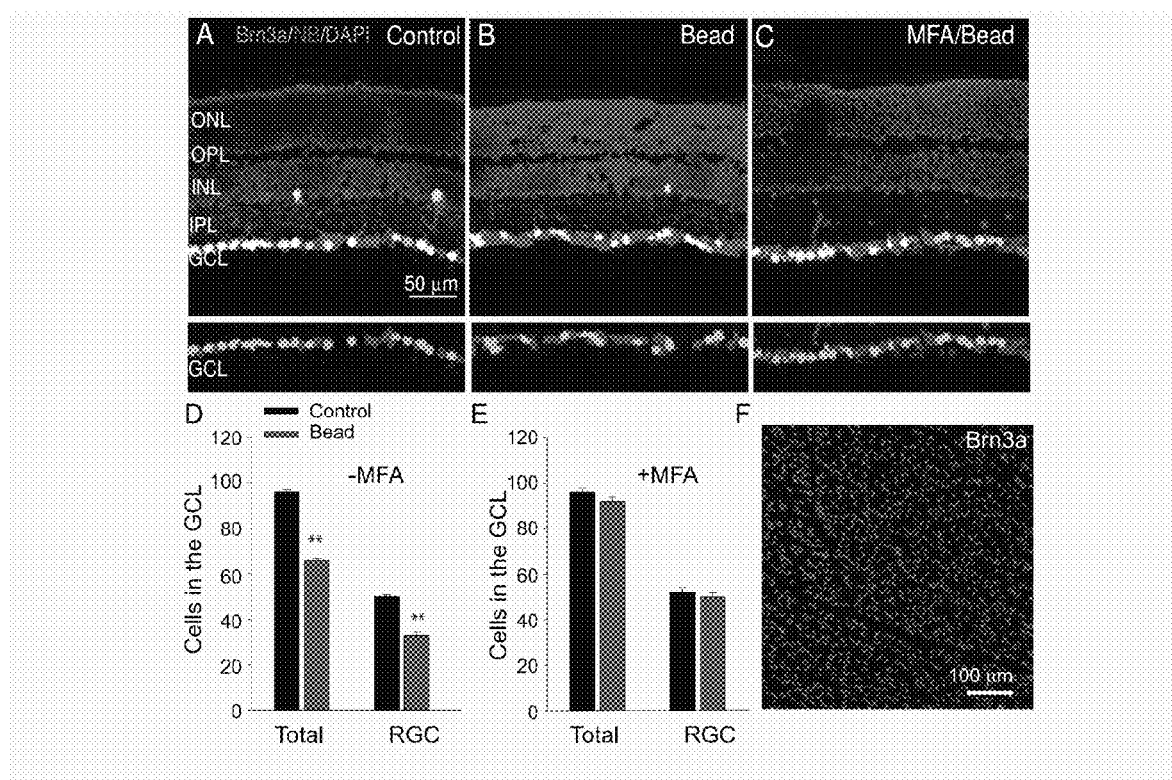
FIGS. 11A-F

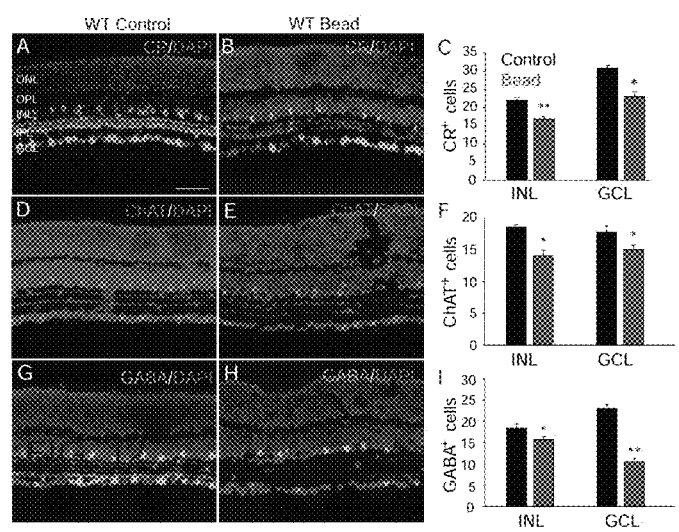
FIGS. 12A-I

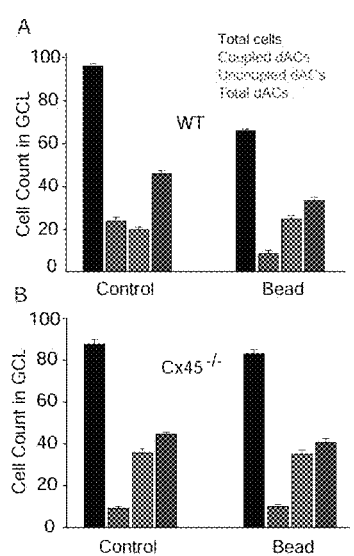
FIGS. 13A-B

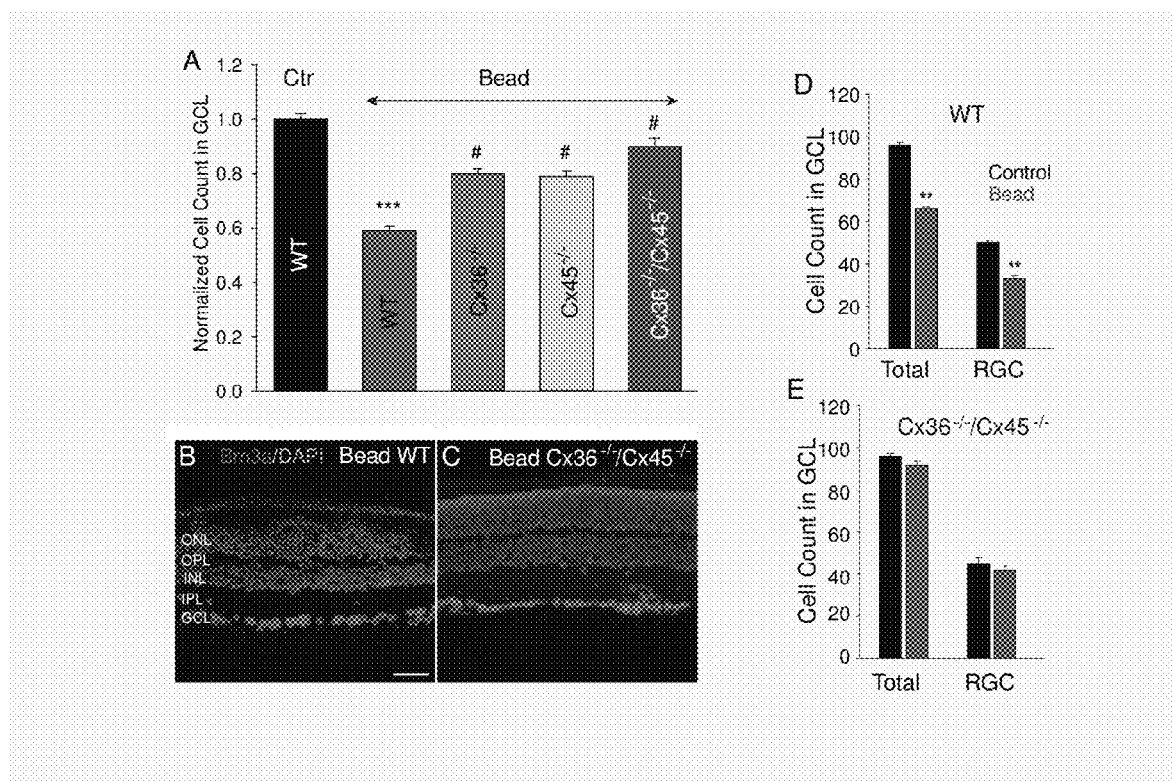
FIGS. 14A-E

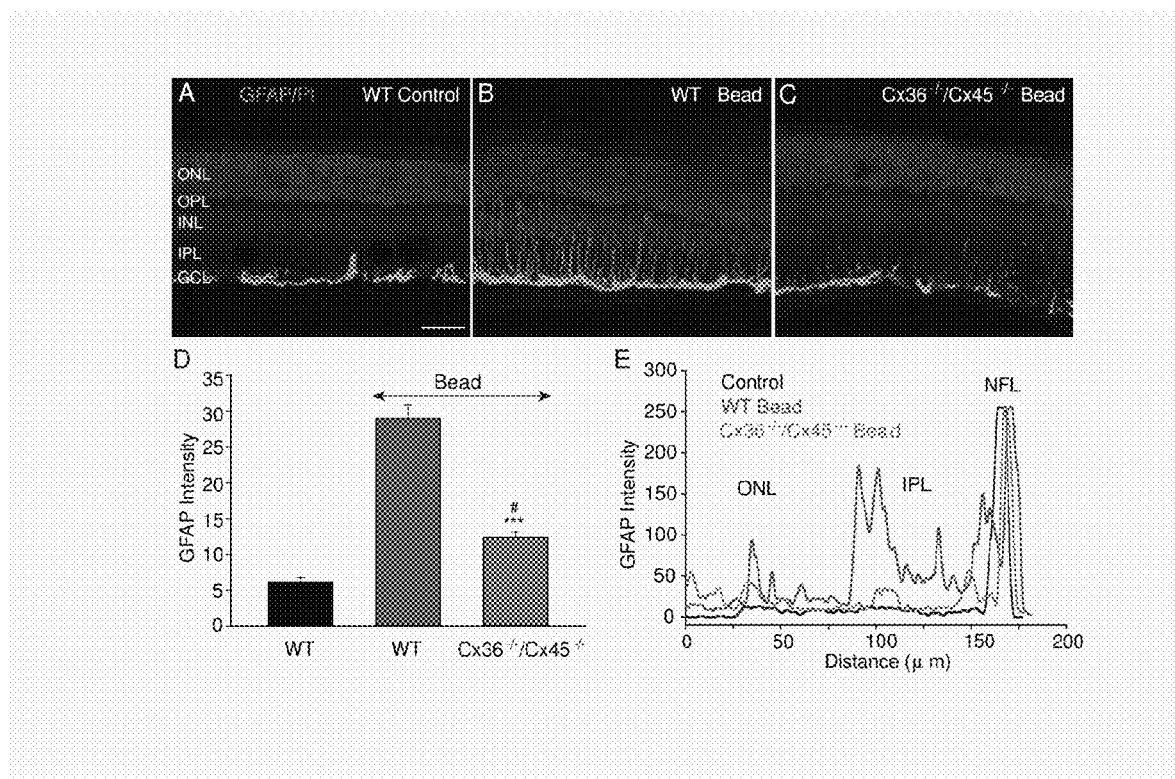
FIGS. 15A-E

METHODS OF USING GAP JUNCTIONS AS THERAPEUTIC TARGETS FOR THE TREATMENT OF DEGENERATIVE DISORDERS OF THE RETINA

CROSS-REFERENCE TO RELATED APPLICATIONS

The present application is a divisional of a co-pending application having U.S. Ser. No. 15/317,171, filed Dec. 8, 2016, which is a 371 of International application having Serial No. PCT/2015/035226, filed Jun. 11, 2015, which claims priority to U.S. provisional application 62/011,354, filed Jun. 12, 2014, which is incorporated herein in its entirety.

STATEMENT REGARDING FEDERALLY SPONSORED RESEARCH OR DEVELOPMENT

This invention was made with government support under grant number R01 EY007360 awarded by the National Institutes of Health. The government has certain rights in the invention.

INCORPORATION BY REFERENCE OF SEQUENCE LISTING

The Sequence Listing in the ASCII text file, named as 31144A_SequenceListing.txt of 12 KB bytes, created on Aug. 24, 2017, and submitted to the United States Patent and Trademark Office via EFS-Web, is incorporated herein by reference.

BACKGROUND OF THE DISCLOSURE

In addition to the intrinsic mechanisms underlying primary cell death, intercellular communication appears to play a major, but presently unclear, role in so-called secondary cell death (Andrade-Rozental A F, et al., Brain Res. Rev 32:308-315 (2000)). Damage in the central nervous system (CNS) leads to the death of a limited cohort of vulnerable cells, which, in turn, pass toxic molecules via gap junctions (GJs) to coupled neighbors. There is now substantial evidence that cells that are clustered and can thereby communicate via GJs tend to die en mass under a broad range of neurodegenerative conditions (Frantseva et al., J. Cereb. Blood Flow Metab. 22:453-462 (2002); Cusato et al., Cell Death Differ 13:1707-1714 (2006); Lei et al., Br J Ophthalmol. 93:1676-1679 (2009); Wang et al., J Neurophysiol 104:3551-3556 (2010). In this scheme, GJs act as portals for the passage of apoptotic signals from injured cells to those to which they are coupled, which can ultimately be the cause of most cell loss (Kenner et al., Cell Tissue Res 298:383-395 (1999); Perez Velazquez et al., Neuroscientist 9:5-9 (2003); Decrock et al., Cell Death Differ 16:524-536 (2009); Belousov and Fontes, Trends Neurosci 36:227-236 (2013)).

There is increasing evidence that GJs are involved in various neurodegenerative ocular disorders, including ischemic retinopathy and glaucoma (Krysko, Apoptosis 10:459-469 (2005); Malone, Glia 55:1085-1098 (2007); Das et al., Biochem Biophys Res Commun 373:504-508 (2008); Kerr et al., J Clin Neurosci 18:102-108(2011); Danesh-Meyer et al., Brain 135:506-520 (2012)). The topography of neuronal loss in the inner retina seen with these pathologies often includes both a diffuse, but clustered pattern suggesting that dying retinal ganglion cells (RGCs) influence neighboring cells, resulting in secondary neuronal degeneration (Levkovitch-Verbin, Invest Ophthalmol Vis Sci 42:975-982 (2001); Lei et al., Br J Ophthalmol. 93:1676-1679 (2009); Vander et al., Curr Eye Res 37:740-748 (2012)). The GJ-mediated secondary cell death, or so-called "bystander effect", has also been implicated in the programmed cell death in the developing retina. Like in the adult, dying cells in developing retina are spatially clustered into distinct networks (Cusato et al., Cell Death Differ 13:1707-1714 (2003); de Rivero Vaccari et al., J. Neurophysiol 98:2878-2886 (2007)). Dopamine, which is a modulator of al communication, as well as the GJ blockers octant and carbenoxolone significantly reduce the rate of programmed and induced cell death in young retinas and the clustering of the remaining dying cells (Varella et al., J Neurochem 73:485-492 (1999); Cusato, Cell Death Differ 13:1707-1714 (2003)).

Amacrine cells (ACs) form the largest cohort of retinal neurons, comprising over 30 distinct morphological subtypes that subserve complex synaptic interactions in the inner plexiform layer (In), which are largely responsible for the diverse physiological properties expressed by RGCs (Demb J B, et al., Vis Neurosci. 29:51-60 (2012)). Studies of glaucomatous human retinas have reported an apparent delayed or secondary degeneration of amacrine cells subsequent to RGC cell loss (Schwartz Eur J Ophthalmol Suppl 3:S27-31 (2002); Kielczewski et al., Invest Ophthahnol Vis Sci 46:3188-3196 (2005); Moon et al., Cell Tissue Res. 320:51-59 (2005)). However, whether ACs are adversely affected in glaucoma remains unclear as conflicting experimental results have been reported (Kielczewski J L, et al., Invest Ophthalmol Vis Sci. 46:3188-96 (2005); GA, Barnett N L., et al. Clin Experiment Ophthalmol. 39:555-63 (2011); Moon J I, et al., Cell Tissue Res. 320:51-9 (2005); Jakobs T C, et al., J Cell Biol. 171:313-25 (2005)).

One explanation for the discrepant findings may be the difficulty in clearly identifying ACs and thereby measuring their loss. For example, in addition to RGCs, displaced amacrine cells (dACs) comprise about 50% of the neurons found in the GCL of the mouse retina (Schlamp C L, et al., Mol Vis. 19:1387-96 (2013)) and no single labeling method can provide complete coverage due to their wide morphological diversity. Interestingly, it has been reported that 16 of the 22 morphological subtypes of RGCs in the mouse retina are coupled to ACs (Völgyi B, et al., J Comp Neurol. 512:664-87 (2009)). This extensive coupling suggests that GJ-mediated secondary cell death would likely progress from RGCs to their coupled AC neighbors or vice versa. A downregulation of calretinin (CR), calbindin (CB), and choline acetyltransferase (ChAT) have been reported in ischemic retinas (Dijk and Kamphius, Brain Res. 1026:194-204 (2004); Bernstein and Guo, Invest Ophthalmol Vis Sci 52:904-910 (2011); Lee et al., Apoptosis 11:1215-1229 (2011)), suggesting that the loss of the AC immunoreactivity may be due to reduced protein detection rather than cell death.

Changes in the expression and function of certain connexin subtypes in CNS have been reported under a variety of pathological conditions (Rouach et al., Biol. Cell. 94:457-475 (2002); Petrash-Parwez et al., J. Comp Neurol 479:181-197 (2004); Eugenin et al., J. Neuroimmune Pharmacol 7:499-518 (2012); Kerr et al., J. Clin Neurosci 28:102-108 (2012)). In addition, the conductance of GJ hemichannels, related to their connexin makeup, appears related to their ability to support bystander cell death (Kameritsch et al., Cell Death Dis 4:1-9 (2013)).

The conductance of GJs, based on their connexin makeup, appears related to their ability to support bystander cell death (Kameritsch P, et al., Cell Death Dis. 4:e584 (2013)).

In addition, changes in the expression of certain connexin subtypes in CNS have been reported under a variety of pathological conditions (Kerr N M, et al., Exp Neurol. 234:144-52, (2012); Rouach N, et al., Biol Cell. 94:457-75 (2002); Petrasch-Parwez et al., J Comp Neurol. 479:181-97 (2004); Eugenin E A, et al., J Neuroimmune Pharmacol. 7:499-518 (2012)).

Thus, the degree to which a particular GJ contributes to secondary cell death is likely dependent on which of the different types of connexin subunits it expresses as well as the insult condition. The fact that at least three connexin subtypes are expressed in the IPL of the retina raises the notion that different cohorts of GJs, based on their connexin profile, may be responsible for secondary cell death in the inner retina arising from different primary insults.

In contrast, some studies have reported that GJs may actually protect cells. Evidence for this "good Samaritan" role include the findings that GJ inhibitors can induce apoptosis (Lee et al., Anat Cell Biol 44:25-34 (2006); Hutnik et al., Invest Ophthalmol Vis Sci 49:800-806 (2008)) and that deletion of GJ connexins can increase neuronal loss (Naus et al., Cell Commun. Adhes 8:325-328 (2001); Striedinger et al., Eur J Neurosci 22:605-6016 (2005)). It has been posited that GJs are portals by which healthy cells provide dying neighbors with rescue signals or that the coupled syncytium can dilute toxic substances (Krysko et al., PLoS One 8:e57163 (2005)). Apoptotic conditions induce various changes in the structure of GJs, including phosphorylation of connexins (Lin et al., Exp Eye Res 85:113-122 (2007)), suggesting that the connexin makeup of a GJ may be a critical factor in determining its contribution to cell death or survival.

The retina displays arguably the highest expression of GJs in the CNS, which are widely distributed amongst the five neuronal types and express a variety of connexin subunits (Bloomfield and Völgyi, Nat Rev Neurosci 10:495-506 (2009)). GJ-mediated secondary cell death has been implicated in retinal neuron loss seen under a number of degenerative conditions, including retinitis pigmentosa, glaucoma, and ischemia (Ripps, Exp Eye Res 74:327-336 (2002); Das et al., Biochem Biophys Res Commun 373:504-508 (2008)). On the other hand, deletion of connexins have failed to increase the survivability of cone photoreceptors in a mouse model of retinitis pigmentosa (Kranz et al., PLoS One 8:e57163 (2013)) and has been reported to increase cell loss after retinal trauma (Striedinger et al., Eur J Neurosci 22:605-6016 (2005)), suggesting that GJs can in fact be neuroprotective.

Thus, the role of retinal GJs in cell death and survival, and in the development or worsening of ocular conditions, remains unclear.

BRIEF SUMMARY OF THE DISCLOSURE

Disclosed herein are methods for treating a condition of the retina, by administering an inhibitor of connexin 36 and/or an inhibitor of connexin 45 to a subject with a retinal condition. In some embodiments, both an inhibitor of connexin 36 and an inhibitor of connexin 45 are administered. The condition of the retina can be selected, for example, from glaucoma, macular degeneration, retinitis pigmentosa, diabetic retinopathy and retinal ischemia.

In any of the above methods, the inhibitor can be selected from an antisense polynucleotide directed to connexin 36 messenger ribonucleic acid (mRNA), an antisense polynucleotide directed to connexin 45 mRNA, and combinations thereof. Preferred antisense polynucleotide inhibitors are those that selectively bind the sequence of SEQ ID NO: 1 or SEQ ID NO: 2. The antisense polynucleotide can be complementary to all of or a portion of connexin 36 mRNA and/or connexin 45 mRNA. The antisense polynucleotide can be the exact complement of all or a portion of connexin 36 mRNA and/or connexin 45 mRNA. The antisense polynucleotide can hybridize to connexin 36 mRNA and/or connexin 45 mRNA with a melting temperature of greater than 20° C., 30° C. or 40° C. under physiological conditions.

Alternatively, the inhibitor can be a small molecule inhibitor. Exemplary small molecule inhibitors include 18-Beta-glycyrrhetinic acid (18Beta-GA or 18β-GA) and meclofenamic acid (MFA).

Any of the above methods can include repeat administration of the inhibitor or inhibitors for a period of one week to one year. Any of the above methods can further include topical administration, such as a drop to be administered to the eye, or intraocular injection.

Further disclosed herein are pharmaceutical compositions for treatment of a retinal condition. The compositions can include an inhibitor of connexin 36 and/or an inhibitor of connexin 45. In one example, the inhibitor or inhibitors can be selected from an antisense molecule directed to connexin 36 mRNA, an antisense molecule directed to connexin 45 mRNA, and combinations thereof. In another example, the composition includes a small molecule inhibitor of connexin 36 and/or a small molecule inhibitor of connexin 45. The small molecule inhibitor or inhibitors can be selected, for example, from 18-Beta-glycyrrhetinic acid (18Beta-GA) and meclofenamic acide (MFA). Any of the disclosed compositions can be formulated for intraocular injection or topical administration to the eye.

Further disclosed herein are uses of any of the disclosed compositions for the treatment of a condition of the retina. In some examples, the condition of the retina can be selected from glaucoma, macular degeneration, retinitis pigmentosa, diabetic retinopathy and retinal ischemia.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1I. Injection of cytochrome C (CytC) into single cells results in GJ-mediated apoptosis of neighboring coupled cells. A-F, Representative photomicrographs of uncoupled (A-C), and coupled (D-F) RGCs in whole mount retina injected with the mixture of Neurobiotin (NB) and CytC to visualize GJ coupling and to induce cell apoptosis, respectively. C, Overlay of panels (A), and (B) shows apoptosis of the impaled RGC (asterisk), but not any neighboring cells. F, Overlay of panels (D) and (E) shows that apoptosis was spread amongst neighboring cells coupled to impaled RGC. G-I, Representative confocal image of coupled Müller cells in retinal vertical section, one of which (asterisk) was injected with NB+ CytC (G) and then labeled with anti-caspase 3 antibody (H) to detect apoptotic cells. (I), Overlay of panels (G) and (H) shows spread of death in coupled neighboring Müller cells. Scale bars=20 µm (A-C and G-I) and 50 m (D-F).

FIGS. 2A-2E. N-methyl-D-aspartate (NMDA)-induced excitotoxic cell death is significantly reduced by gap junction blockers. (A, C), NMDA-induced cell death in the GCL of control retinas, and those treated for 30 min with 25 µM of 18β-GA (B), or 50 µM of MFA (D) prior exposing to NMDA (300 µM). In experiments illustrated on upper panels, live and dead cells are marked with calcein-AM (green) and ethidium homodimer (EthD, red), respectively. In experiments on lower panels, retrograde labeling through optic nerve cut with LY was used to label RGCs and then retinas processed with EthD to detect dead cells. (E), Histogram summarizes the protective effect of GJ blockers on RGCs against NMDA-induced excitotoxicity. The number of dead cells was counted manually per unit area from 5 different visual fields in the GCL of whole-mount retinas pretreated with 18β-GA (n=12/3), or MFA (n=42/5), and numbers were normalized to one obtained in retinas exposed to NMDA alone (control, n=44/5). **$p<0.001$ vs. control. Scale bar=100 μm.

FIGS. 3A-3E. Blockade of GJs reduced retinal injury and cell death following ischemia-reperfusion. (A) In control retinas, glial fibrillary acidic protein (GFAP) expression was confined exclusively to astrocytes in the GCL and nerve fiber layer (NFL). (B) Seven days after reperfusion the inner retinal thickness was reduced and the GFAP immunoreactivity appeared to traverse throughout the retinal layers and in the Müller cell processes. (C), Intravitreal injection of MFA (500 μM, 2 μl) prevented changes in the retinal morphology and reduced GFAP immunoreactivity. (D) Histogram shows the nuclear counts in the GCL of vertical sections of control (n=19/5; sections/retinas), and ischemic retinas in the presence (n=16/5) or absence (n=16/5) of MFA. (E) Histogram quantifies the GFAP immunofluorescence intensity throughout the vertical section in control and ischemic retinas with or without MFA treatment. MFA was injected intravitreally either once 30 min before (blue, n=16/5), or twice at 3 and 24 hours after (yellow, n=12/3) ischemic insult vs. untreated ischemic retina). Retinal sections were counterstained with PI. *$p<0.01$. Scale bar=50 μm.

FIGS. 4A-4G. Visualization of AC subpopulations with low and high degrees of coupling to retrograde labeled RGCs. (A, C), Retinal GCs in control eyes were retrograde labeled for 40 min with NB, and double labeled with antibodies against amacrine cell marker calretinin (CR), or choline acetyltransferase (ChAT). Cells positive to both NB and corresponding AC markers are shown by arrowheads. (B, D), Blockade of GJs with MFA significantly reduced the number of Neurobiotin-labeled, DR-IR amacrine cells in the INL, but had little effect on ChAT-IR cell numbers. (E), Histogram shows that while the total number of CR-IR cells (per 500 μm section) in the inner nuclear layer (INL) of MFA-treated retinas was comparable to that in control (n=18/4, $p>0.1$), the number of those labeled with Neurobiotin was significantly reduced by MFA-treatment (n=8/3). (F), There was no significant difference in the number of NB-positive ChAT-IR cells in control (n=16/3), and MFA-treated retinas (n=6/3, $p>0.1$). (G), Histogram quantifying the percentage of CR-IR and ChAT-IR amacrine cells in the INL that are coupled to RGCs under control conditions. *$p<0.01$. Scale bars=50 μm.

FIGS. 5A-5L. Amacrine cells that are extensively coupled to RGCs show higher susceptibility to NMDA-induced excitotoxicity. (A), Calretinin (CR) labels a large number of cells in the INL and GCL of control retina. (B), In retinas exposed for 1 h to NMDA (300 μM), the number of CR-positive cells was significantly reduced. (C), In vitro treatment of retinas with MFA (50 μM, 30 min) prevented reduction in the number of CR-IR cells in the INL. (D), Histogram summarizing NMDA-induced changes in the number of CR-positive ACs in the INL of untreated (n=18/3) and MFA-treated retinas (n=10/3). (E), Calbindin (CB) labeled horizontal cells in control retina. (F), Exposure to NMDA reduced the number of CB-IR cells in the proximal INL. (G), Blockade of GJs with MFA prevented such reduction. (H), Histogram summarizing NMDA-induced changes in the number of CB-positive ACs in the INL of untreated (n=22/3) and MFA treated retinas (n=6/3). The number of ChAT-IR ACs in control retinas (I-L), No significant change in the number of ChAT-IR ACs was observed in NMDA-treated retinas compared to controls (n=20/4). Retinal sections were counterstained with PI. *$p<0.01$ vs. control. Scale bars=50 μm.

FIGS. 6A-6L. Amacrine cells with a high degree of coupling to RGCs show higher susceptibility to ischemia-reperfusion injury. (A-C), Calretinin-IR cells in control retinas and in those subjected to ischemia-reperfusion injury in the absence and presence of MFA. (D), Histogram summarizing alteration in the number of CR-IR ACs in the INL of ischemic retinas with (n=26/5) or without (n=48/5) MFA-treatment. (E), Calbindin (CB) immunoreactivity was localized to the horizontal cells and ACs in the INL and sparse GCs. Three strata in the IPL were labeled as well. (F), Changes in retinal morphology and the number of CB-IR cells following ischemia/reperfusion. (G), Blockade of GJs by MFA largely prevented a reduction in the number of CB-IR cells. (H), Histogram summarizing changes in CB-IR cells in the INL of control and ischemic retinas untreated (n=17/3), or treated (n=21/3) with MFA. (I-L), No detectable change in the number of ChAT-IR ACs was observed in ischemic retinas compared to levels in controls (n=25/4 each, $p>0.1$). Retinal sections were counterstained with PI. *$p<0.001$ vs. control. Scale bars=50 μm.

FIGS. 7A-7E. Gap junctions formed by Cx36 mediate bystander cell death under excitotoxic conditions. (A-D), Neuronal death was measured by EthD staining in whole-mount retinas of heterozygous (Het), $Cx36^{-/-}$, $Cx36^{-/-}/45^{-/-}$ double knock-out (dKO), and $Cx45^{-/-}$ mice. (E), Histogram quantifying excitotoxic cell death in the GCL of retinas from Het and connexin knock out (KO) mice. Compared to Hets (n=35/3), the reduction in NMDA-induced cell death was statistically significant in retinas of $Cx36^{-/-}$ (n=35/3), and $Cx36^{-/-}/Cx45^{-/-}$ dKO (n=13/3) mice, but not in $Cx45^{-/-}$ (n=17/3; $p>0.1$). *$p<0.001$ vs. Het. Scale bar=50 μm.

FIGS. 8A-8J. Gap junctions formed by Cx45 mediate bystander cell death under ischemic conditions. (A), lucifer yellow (LY) retrogradely labeled RGC somas and their axons in control retina of Het mouse, ischemic Het retina (B), $Cx36^{-/-}$ retina (C), and $Cx45^{-/-}$ retina (D). (E), Immunoreactivity of GFAP in vertical sections of control retina and ischemic retinas of Het (F), $Cx36^{-/-}$ (G), and $Cx45^{-/-}$ (H) mice. Following ischemia-reperfusion, the GFAP immunoreactivity was upregulated throughout the retinal layers of Het and $Cx36^{-/-}$, but not $Cx45^{-/-}$ mice. (I), Histogram shows the nuclear cell count (per 500 μm length of vertical sections) in the GCL of control (n=54/5), and ischemic retinas of Het (n=28/3), $Cx36^{-/-}$ (n=24/4) and $Cx45^{-/-}$ (n=74/5) mice. (J), Quantification of GFAP immunofluorescence intensity in the ischemic retinas of Het (n=24/4), $Cx36^{-/-}$ (n=24/4), and $Cx45^{-/-}$ (n=22/4, $p>0.1$) mice. *$p<0.001$ vs. control. Scale bars=100 μm (A-D), 50 μm (E-H).

FIGS. 9A-9L. Changes in the immunolabeling of Cx36 and Cx45 in the IPL of retinas subjected to excitotoxic or ischemic insults. (A), In control retina Cx36 immunoreactivity appeared as punctate labeling predominantly in the inner half of the IPL. (B), In ischemic retinas the punctuate pattern of Cx36 labeling appeared as large clusters surrounding the cell nucleus. (C), NMDA-induced excitotoxicity had little effect on the pattern of Cx36 immunolabeling. (D), Histogram shows significant reduction in the intensity of punctate Cx36 immunoreactivity in the IPL of ischemic retinas (n=7/3) compared to that in controls (n=21/3). No detectable change in the Cx36 immunolabeling was observed under excitotoxic conditions (n=8/3). (E), There was no significant difference in NMDA-induced cell death in the Het and Cx36$^{-/-}$ retinas (n=21/3; p>0.1). (F), NMDA-induced cell death was significantly less in Cx36$^{-/-}$ (n=35/3) compared to Het retina (n=14/3). (G), Punctate immunolabeling for Cx45 was observed throughout the IPL of control retina. (H), The punctuate pattern and the intensity Cx45 labeling were not altered by ischemia-reperfusion. I, NMDA markedly reduced Cx45 immunolabeling. (J), Histogram quantifies Cx45 immunoreactivity in the IPL of retinas exposed to NMDA (n=8/4), compared to those in control (n=28/4), and ischemic retinas (n=26/4). (K), Cell death was significantly less in ischemic retinas of Cx45$^{-/-}$ mice (n=24/5) as compared to that in Het mice (n=30/5). (L), There was no statistically significant difference in NMDA-induced cell death between Het and Cx45$^{-/-}$ retinas (n=18/3, p>0.1). **p<0.001. *p<0.01. Scale bars=20 μm.

FIGS. 10A-10D. Elevation of intraocular pressure (IOP) and progressive cell loss in an experimental model of glaucoma induced by microbead injection into the eye. (A), Mean IOP measured over an 8 week period following injection of microbeads (red) or control phosphate buffered saline (PBS) (black) into eyes of wild type (WT) mice. The elevated IOP produced by microbead injection started to decline at 2 weeks and so a second injection was performed at 4 weeks following initial procedure. (B), Expression of GFAP in control retinas was limited mainly to astrocytes in the GCL and nerve fiber layer (NFL). Calibration bar for B=50 μm and pertains to C as well. (C), Eight weeks after microbead injection, the GFAP expression expanded to Müller cell processes that extended vertically through the retinal layers. (D), Normalized cell counts in the GCL (per 630 μm length) of retinal sections made under control conditions and 1, 4 and 8 weeks after first microbead injection. There was a 20% decrease in total cell count in the GCL at 4 weeks and a 36% decrease at 8 weeks after microbead injection compared to control values. Bars represent mean±SD. p<0.01; *p<0.001 (Student's t-test).

FIGS. 11A-11F. Blockade of gap junctions with MFA prevents loss of cells in GCL in microbead-injected eyes. Pharmacological blockade of GJs with MFA promotes RGC protection in experimental glaucoma. (A), Vertical sections of retinas from WT mice under control conditions and those subjected to microbead injection without (B), or with (C) intravitreal injection of MFA. Under control conditions or 8 weeks after the initial microbead injection, eyes were retrogradely labeled with Neurobiotin (red), to visualize RGCs and the ACs and dACs to which they are coupled via GJs. Sections were then subsequently immunolabeled for Brn3a (green), to identify RGCs, and counter-stained with the nuclear fluorogen 4',6-diamidino-2-phenylindole (DAPI) (blue), to visualize nuclei of all cells for cell counts. D-E. Histograms comparing the total cell (RGC+dAC) and RGC counts in the GCL of microbead-injected retinas from WT mice untreated (D) or treated with MFA (E) to block GJs. Microbead injection clearly induced cell loss in the GCL, but blockade of GJs prevented the loss. (F), Brn3A immunolabeling of RGCs in flat mount view. Calibration bar in A=50 μm and pertains to B and C. Cell counts are per 1.3 mm length of retinal section. Bars represent mean±standard error of the mean (SEM). **p<0.01 (Student's t-test).

FIGS. 12A-12I. Experimental glaucoma results in cell loss with AC populations. Immunolabels for AC populations, including CR, ChAT, and GABA were made in retinas of WT mice under control conditions (A, D, G) and 8 weeks after initial microbead injection (B, E, H). Cell counts were carried out in both the INL for ACs and GCL for dACs in vertical sections (C, F, I). There was a significant reduction of cells within all the different populations of ACs/dACs after microbead injection. Cells counts are per 630 μm length of retinal section. Calibration bar in A=50 μm and pertains to B-H. Histogram bars represent mean±SEM. *p<0.05, **p<0.01 (Student's t-test).

FIGS. 13A-13B. Ablation of Cx45 prevents loss of coupled dACs in experimental glaucoma. Cell counts of total cells in the GCL based on DAPI label and coupled and uncoupled dACs taken as those labeled by retrograde Neurobiotin injection and those not labeled by Neurobiotin nor Brn3a, respectively. Counts were made in WT (A) and Cx45$^{-/-}$ mice (B) under control conditions and 8 weeks after initial microbead injection. Microbead injection resulted in a loss of coupled dACs, but there was a small increase in uncoupled dACs. However, there was no loss in coupled or uncoupled dACs in the Cx45$^{-/-}$ mouse retinas. Bars represent mean±SEM. Differences in cell count values between control and microbead-injected WT mice were all significant (p<0.05; Students t-test). None of the differences in cell count values between control and microbead-in-jected Cx45-/- mice were significant (p>0.1 for each, Students t-test).

FIGS. 14A-14E. Genetic ablation of Cx36, Cx45 or both Cx36/45 significantly reduces cell loss in experimental glaucoma. (A), Normalized (to control) total cell counts in the GCL of WT under control conditions and WT and connexin KO mice retinas 8 weeks after initial microbead injection to elevate IOP. There was a decrease in cell loss of 45% and 50%, respectively, in Cx36$^{-/-}$ and Cx45$^{-/-}$ glaucomatous mouse retinas compared to values in glaucomatous WT retinas. We observed a 94% reduction in cell loss in glaucomatous Cx36$^{-/-}$/Cx45$^{-/-}$ retinas indicating an additive effect of ablating both connexins. (B-C), Confocal images of vertical sections immunolabeled with Brn3a illustrating a significant protection of RGCs in microbead-injected retinas of Cx36$^{-/-}$/Cx45$^{-/-}$ mouse retina compared to WT. Calibration bar in B=50 μm and pertains to C as well. (D-E), Histograms showing changes in the number of total cells and RGCs in the GCL in WT and Cx36$^{-/-}$/Cx45$^{-/-}$ mice under control conditions and 8 weeks after initial microbead injection. Total cells counts were based on measures of DAPI-positive nuclei in the GCL. Values represent mean±SEM **p<0.01 (Student's t-test).

FIGS. 15A-15E. Injury-induced GFAP expression in the retina following microbead injection is significantly reduced by deletion of Cx36 and Cx45. (A), Before microbead injection, GFAP expression in WT mouse retinas is restricted to astrocytes and end feet of the Müller cells at the inner limiting membrane. (B), Eight weeks after microbead injection there is an upregulation of GFAP in Müller cell processes that span the retinal layers. (C), This increase in GFAP expression was not seen in Cx36$^{-/-}$/Cx45$^{-/-}$ retinas 8 weeks after initial microbead injection indicating a decrease in retinal injury. (D-E), Curves quantifying the expression of GFAP in the retinas of the WT and KO mice under control and microbead-injected conditions. The profiles show a clear reduction in GFAP in the IPL of KO mice as compared to values in the WT after induction of experimental glaucoma. Scale bar in A=50 μm, and pertains to B and C as well. Values represent mean±SEM **p<0.01 (Student's t-test).

DETAILED DESCRIPTION OF THE DISCLOSURE

Disclosed herein are methods for treating a condition of the retina by administration of an inhibitor of connexin-36 and/or an inhibitor of connexin-45 to a subject who could benefit from the administration thereof.

The disclosure provides results of a comprehensive study of the role of gap junctions (GJs) in secondary neuronal death in the retina initiated by excitotoxic or ischemic conditions. Significant numbers of retinal ganglion cells are lost followed by subsequent loss of coupled amacrine cells after being subjected to excitotoxic or ischemic conditions. However, in accordance with the present disclosure, pharmacological blockade of gap junctions or genetic deletion of connexins increased survivability of neurons by up to about 90%. The disclosure provides methods of targeting specific connexins to reduce progressive cell loss initiated by diverse neurodegenerative conditions. Moreover, the present disclosure reveals that apoptosis in a single cell can spread to neighboring cells via functional gap junctions and furthermore that gap junctions mediate secondary cell-death in a connexin-specific manner. Therefore, in accordance with the present disclosure, it has been determined that gap junctions represent a novel, important target for neuroprotection.

The inventors have investigated the hypothesis that GJ-mediated secondary cell death forms a principle mechanism for the progressive loss of cells under experimental glaucoma. The inventors have discovered that secondary or "bystander" cell death via GJs play a critical role in the progressive loss of retinal ganglion cells (RGCs) and amacrine cells (ACs) in retinal conditions such as glaucoma. This disclosure reveals the unexpected vulnerability of RGCs and ACs in glaucoma, the role of GJ coupling in the progression of cell loss, and which GJs, based on their connexin make-up, can be targeted to protect cells. This disclosure thus defines a new mechanism for retinal bystander cell death, and thus provides novel therapeutic targets for neuroprotection to preserve cell health and visual function in glaucomatous retinas. This level of analysis of the bystander effect has not been previously performed at any CNS locus. The retina, due to its GJ diversity, offers a unique venue to study this mechanism. Provided are treatments for many neurodegenerative diseases of the retina, such as glaucoma, retinitis pigmentosa and ischemic retinopathy, as well as those associated with other CNS loci.

Connexins, or gap junction proteins, are a family of structurally related transmembrane proteins that assemble to form vertebrate gap junctions. Connexins are four-pass transmembrane proteins with cytoplasmic C- and N-termini, a cytoplasmic loop (CL) and two extra-cellular loops, (EL-1) and (EL-2). Connexins assemble into groups of six to form hemichannels, or connexons, and two hemichannels then combine to form a gap junction. The connexin gene family is diverse, with twenty-one identified members in the sequenced human genome, and twenty in the mouse. The various connexins have been observed to combine into both homomeric and heteromeric gap junctions, each of which may exhibit different functional properties including pore conductance, size selectivity, charge selectivity, voltage gating, and chemical gating, depending at least in part on the combination of connexins present in the GJ.

Connexin 36 (Cx36), also known as gap junction protein delta 2, is a connexin with the nucleic acid sequence of SEQ ID NO: 1. The nucleic acid and amino acid sequence of Cx36 are available at Genbank Accession No. NM_020660. Connexin 45 (Cx45), also known as gap junction protein, gamma 1, is a connexin with the nucleic acid sequence of SEQ ID NO: 2. The nucleic acid and amino acid sequence of Cx45 are available at Genbank Accession No. NM_005497.

Accordingly, disclosed herein are methods for treating a condition of the retina, by administering an inhibitor of connexin 36 and/or an inhibitor of connexin 45 to a subject with a retinal condition. In some embodiments, both an inhibitor of connexin 36 and an inhibitor of connexin 45 are administered. The condition of the retina can be selected, for example, from glaucoma, macular degeneration, retinitis pigmentosa, diabetic retinopathy and retinal ischemia.

In any of the above methods, the inhibitor can be selected from an antisense molecule directed to connexin 36 mRNA, an antisense molecule directed to connexin 45 mRNA, and combinations thereof. Preferred antisense molecule inhibitors are those that selectively bind the mRNA sequence of connexin 36 (SEQ ID NO: 1) or the mRNA sequence of connexin 45 (SEQ ID NO: 2).

A "connexin inhibitor" is a molecule that modulates or down-regulates one or more functions or activities of a connexin or a connexin hemichannel (connexon) comprising a connexin of interest. Connexin inhibitors include, without limitation, antisense compounds (e.g., antisense polynucleotides), RNA interference (RNAi) and small interfering RNA (siRNA) compounds, antibodies and binding fragments thereof, and peptides and polypeptides (including "peptidomimetics" and peptide analogs). Preferred connexin inhibitors are inhibitors of connexins found in neural GJs. Most preferred are inhibitors of connexin 36 and/or connexin 45. In one embodiment, the connexin inhibitors of the present invention can modulate or prevent the transport of molecules, particularly molecules that initiate cell death, into and out of neural cells.

Certain connexin inhibitors provide downregulation of connexin expression, for example, by downregulation of mRNA transcription or translation, or decrease or inhibit a connexin protein, a connexin hemichannel or neural signaling activity (Asazuma-Nakamura et al, *Exp Cell Res.*, 2009, 315: 1190-1199; Nakano et al., *Invest Ophthalmol Vis Sci.*, 2007, 49: 93-104; Zhang et al., *Oncogene,* 2001, 20: 4138-4149).

Anti-connexin polynucleotides include connexin antisense polynucleotides as well as polynucleotides having functionalities that enable them to downregulate connexin expression. Other suitable anti-connexin polynucleotides include RNAi polynucleotides, siRNA polynucleotides, and short hairpin RNA (shRNA) polynucleotides.

Synthesis of antisense polynucleotides and other anti-connexin polynucleotides (RNAi, siRNA, and ribozyme polynucleotides as well as polynucleotides having modified and mixed backbones) is known to those of skill in the art. See, e.g., Stein C. A. and Krieg A. M. (Eds.), Applied Antisense Oligonucleotide Technology, 1998 (Wiley-Hiss). Methods of synthesizing antibodies and binding fragments as well as peptides and polypeptides (including peptidomimetics and peptide analogs) are known to those of skill in the art. See, e.g., Lihu Yang et al., *Proc. Natl. Acad. Sci. U.S.A.*, 1; 95(18): 10836-10841 (Sep. 1, 1998); Harlow and Lane (1988) "Antibodies: A Laboratory Manual" Cold Spring Harbor Publications, New York; Harlow and Lane (1999) "Using Antibodies" A Laboratory Manual, Cold Spring Harbor Publications, New York.

In one example, the downregulation of connexin expression is enacted by use of antisense polynucleotides (such as DNA or RNA polynucleotides), and more particularly upon the use of antisense oligodeoxynucleotides (ODN). These polynucleotides (e.g., ODN) target the connexin protein(s) to be downregulated. Typically, the polynucleotides are single-stranded, but may be double-stranded.

The antisense polynucleotide may inhibit transcription and/or translation of a connexin. Preferably, the polynucleotide is a specific inhibitor of transcription and/or translation from the connexin gene or mRNA, and does not inhibit transcription and/or translation from other genes or mRNAs. The product may bind to the connexin gene or mRNA either 5' to the coding sequence; and/or within the coding sequence, and/or 3' to the coding sequence. Administration of such connexin-targeted antisense polynucleotides inhibits bystander cell death in the retina.

The antisense polynucleotide is generally antisense to a connexin mRNA. Such a polynucleotide may be capable of hybridizing to the connexin mRNA, and may thus inhibit the expression of connexin by interfering with one or more aspects of connexin mRNA metabolism (including transcription, mRNA processing, mRNA transport from the nucleus, translation or mRNA degradation). The antisense polynucleotide typically hybridizes to the connexin mRNA to form a duplex that can cause direct inhibition of translation and/or destabilization of the mRNA. Such a duplex may be susceptible to degradation by nucleases.

The antisense polynucleotide may hybridize to all or part of the connexin mRNA. Typically, the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required, and polynucleotides that have sufficient complementarity to form a duplex having a melting temperature of greater than about 20° C., 30° C. or 40° C. under physiological conditions (that is, under standard cellular conditions of salt, pH, etc., such as 0.09-0.15 M sodium phosphate, pH 6.5-7.2) are particularly suitable for use in the present invention.

Thus, the polynucleotide is typically a homologue of a sequence complementary to the mRNA. The polynucleotide may be a polynucleotide that hybridizes to the connexin mRNA under conditions of medium to high stringency, such as 0.03 M sodium chloride and 0.03 M sodium citrate at from about 50° C. to about 60° C.

For certain aspects, suitable polynucleotides are typically from about 6 to 40 nucleotides in length. Preferably, a polynucleotide may be from about 12 to about 35 nucleotides in length, or more preferably from about 18 to about 32 nucleotides in length. According to another aspect, the polynucleotide may be at least about 40, for example, at least about 60 or at least about 80 nucleotides in length; and up to about 100, about 200, about 300, about 400, about 500, about 1,000, about 2,000 or about 3,000 or more nucleotides in length.

In one preferred aspect, the antisense polynucleotides are targeted to the mRNA of only one connexin protein. Most preferably, this connexin protein is connexin 36 or 45. Polynucleotides targeted to connexins 36 and 45 proteins may be used in combination. In addition, antisense nucleotides targeted to connexins 36 and 45, in combination with antisense nucleotides targeted to one or more additional connexin proteins (such as connexins 26, 30, 30.3, 31.1, 32, 37, 40, 43, 45, and 47), are used. These are examples of human connexin proteins. In the case of other animal species, mRNA of the corresponding connexin is targeted. In one embodiment, the combination of antisense nucleotides does not include an antisense nucleotide targeted to connexin 43.

Individual antisense polynucleotides may be specific to connexin 36 or 45, or may hybridize to connexin 36 and/or 45 and 1, 2, 3 or more additional connexins. Specific polynucleotides will generally target sequences in the connexin gene or mRNA that are not conserved between connexins, whereas non-specific polynucleotides will target conserved sequences for various connexins.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates, and their 2'-O-alkyl analogs and 2'-O-methylribonucleotide methylphosphonates. Alternatively, mixed backbone oligonucleotides ("MBOs") may be used. MBOs contain segments of phosphorothioate oligodeoxynucleotides and appropriately placed segments of modified oligodeoxy- or oligoribonucleotides. MBOs have segments of phosphorothioate linkages and segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

Polynucleotides (including ODNs) directed to connexin proteins can be selected in terms of their nucleotide sequence by any suitable approach. For example, the computer programs MacVector and OligoTech (from Oligos Etc., Eugene, Oreg., USA) can be used. Once selected, the ODNs can be synthesized using a DNA synthesizer.

For example, the polynucleotide may be a homologue of a complement to a sequence of connexin 36 or connexin 45 mRNA. Such a polynucleotide typically has at least about 70% homology, preferably at least about 80%, at least about 90%, at least about 95%, at least about 97%, at least about 98% or at least about 99% homology with a portion of SEQ ID NO: 1 or SEQ ID NO: 2, for example, over a region of more than at least about 15, at least about 20, at least about 40, or at least about 100 contiguous nucleotides of SEQ ID NO: 1 or SEQ ID NO: 2.

Homology may be calculated based on any method in the art. For example, the UWGCG Package provides the BEST-FIT program, which can be used to calculate homology (for example, used on its default settings) (Devereux et al. (1984) *Nucleic Acids Research* 12, p 387-395). The PILEUP and basic local alignment search tool (BLAST) algorithms can be used to calculate homology or line up sequences (typically on their default settings), for example, as described in Altschul, S. F. (1993) *J Mol Evol* 36: 290-300; Altschul, S. F. et al. (1990) *J Mol Biol* 215: 403-10.

Software for performing BLAST analyses is publicly available online through the National Center for Biotechnology Information. This algorithm involves first identifying high-scoring sequence pairs (HSPs) by identifying short words of length W in the query sequence that either match or satisfy some positive-valued threshold score T when aligned with a word of the same length in a database sequence. T is referred to as the neighborhood word score threshold (Altschul, S. F. (1993) *J Mol Evol* 36: 290-300; Altschul, S. F. et al. (1990) *J Mol Biol* 215: 403-10). These initial neighborhood word hits act as seeds for initiating searches to find HSPs containing them. The word hits are extended in both directions along each sequence for as far as the cumulative alignment score can be increased. The BLAST algorithm parameters W, T and X determine the sensitivity and speed of the alignment. The BLAST program uses as defaults a word length (W), the BLOSUM62 scoring matrix (Henikoff and Henikoff (1992) *Proc. Natl. Acad. Sci USA* 89: 10915-10919), alignments (B) of 50, expectation (E) of 10, M=5, N=4, and a comparison of both strands.

The BLAST algorithm performs a statistical analysis of the similarity between two sequences. See, e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example, 0.03M sodium chloride and 0.03 M sodium citrate at from, about 50° C. to about 60° C.). However, such hybridization may be carried out under any suitable conditions known in the art (see Sambrook et al. (1989), Molecular Cloning: A Laboratory Manual). For example, if high stringency is required, suitable conditions include 0.2×SSC at 60° C. If lower stringency is required, suitable conditions include 2×SSC at 60° C.

Alternatively, the inhibitor can be a small molecule inhibitor or a connexin binding protein (including peptides, peptidomimetics, antibodies, antibody fragments, and the like). The term "small molecule" as used herein refers to molecules that exhibit a molecular weight of less than 5000 Da, more preferred less than 2000 Da, even more preferred less than 1000 Da and most preferred less than 500 Da. Compounds or competitor compounds that are synthetic and/or naturally occurring "small molecule" compounds, e.g. drugs, metabolites, prodrugs, potential drugs, potential metabolites, potential prodrugs and the like, are preferred for use in the methods described and claimed herein. Preferably, said compounds or competitor compounds are selected from the group consisting of synthetic or naturally occurring chemical compounds or organic synthetic drugs, more preferably small molecules, organic drugs or natural small molecule compounds. Exemplary small molecule inhibitors include 18-Beta-glycyrrhetinic acid (18Beta-GA) and meclofenamic acid (MFA). Small molecule inhibitors may be screened from small molecule libraries available in the art for ability to inhibit connexin 36 and/or connexin 45.

Further disclosed herein are use of inhibitors of connexin 36 and/or connexin 45, including, but not limited to, antisense polynucleotides, RNAi and siRNA compounds, antibodies and binding fragments thereof, peptides and polypeptides, and small molecules, in the preparation of a pharmaceutical composition for the treatment of retinal conditions, such as glaucoma, macular degeneration, retinitis pigmentosa, diabetic retinopathy and retinal ischemia. Additionally disclosed are methods of treatment for retinal conditions, involving administration of inhibitors of connexin 36 and/or connexin 45.

As used herein, "treatment" refers to clinical intervention in an attempt to alter the disease course of the individual or cell being treated, and can be performed either for prophylaxis or during the course of clinical pathology. Therapeutic effects of treatment include without limitation, preventing occurrence or recurrence of disease, alleviation of symptoms, diminishment of any direct or indirect pathological consequences of the disease, decreasing the rate of disease progression, amelioration or palliation of the disease state, and remission or improved prognosis.

Any of the above methods can include repeat administration of the inhibitor or inhibitors for a period of 1 week to 1 year, such as 1-4 weeks, 1-3 months, 1-6 months, 6 months to 1 year, or a year or more. Administration can be, for example, one, two, or three times daily, once every 2-3 days, or once per week. Particularly contemplated is topical administration, such as a drop to be administered to the eye. Topical administration includes directly applying, laying, or spreading on or around the eye, e.g., by use of an applicator such as a wipe, a contact lens, a dropper, or a spray.

Also disclosed herein are pharmaceutical compositions for treatment of a retinal condition. The compositions include an inhibitor of connexin 36 and/or an inhibitor of connexin 45. The inhibitor or inhibitors can be selected from an antisense molecule directed to connexin 36 mRNA, an antisense molecule directed to connexin 45 mRNA, and combinations thereof. In another example, the composition includes a small molecule inhibitor of connexin 36 and/or a small molecule inhibitor of connexin 45. In a further example, the inhibitor or inhibitors can be selected from 18-Beta-glycyrrhetinic acid (18Beta-GA) and meclofenamic acide (MFA). Any of the disclosed compositions can be formulated for topical administration or intraocular injection to the eye.

Particularly contemplated are compositions that include an inhibitor of connexin 36 and/or an inhibitor of connexin 45 in a pharmaceutically acceptable carrier. As used herein, the phrase "pharmaceutically acceptable" means the carrier, or vehicle, does not cause an adverse reaction when administered to a mammal. Such carriers are non-toxic and do not create an inflammatory or anergic response in the body. Pharmaceutically acceptable carriers for practicing the invention include well known components such as, for example, culture media and phosphate buffered saline. Additional pharmaceutically acceptable carriers and their formulations are well-known and generally described in, for example, Remington's Pharmaceutical Science (18th Ed., ed. Gennaro, Mack Publishing Co., Easton, Pa., 1990) and the Handbook of Pharmaceutical Excipients (4th ed., Ed. Rowe et al. Pharmaceutical Press, Washington, D.C.), each of which is incorporated by reference.

A composition containing an inhibitor of connexin 36 and/or an inhibitor of connexin 45 can be formulated for topical administration. Forms of the composition include, but are not limited to, solutions, ointments, gels, emulsions, suspensions, gel shields, and the like. In one embodiment, the composition is formulated as an aqueous-based cream excipient, which can be applied to the eye at bedtime, but may also be applied any time throughout the day. In another embodiment, the composition is formulated as a solution or suspension and is applied topically in the form of eye drops. Any solution suitable for topical application in which a disclosed inhibitor is soluble can be used; e.g., sterile water, Sorenson's phosphate buffer, and the like.

In other embodiments, a composition is formulated to have properties such as sustained-release or improved stability. For example, a polymeric matrix composition containing an inhibitor of connexin 36 and/or an inhibitor of connexin 45 can be topically applied to the eye to achieve sustained release.

Compositions containing an inhibitor of connexin 36 and/or an inhibitor of connexin 45 can include additional ingredients, additives or carrier suitable for use in contact on or around the eye without undue toxicity, incompatibility, instability, irritation, allergic response, and the like. Additives such as solvents, bases, solution adjuvants, suspending agents, thickening agents, emulsifying agents, stabilizing agents, buffering agents, isotonicity adjusting agents, soothing agents, preservatives, corrigents, olfactory agents, coloring agents, excipients, binding agents, lubricants, surfactants, absorption-promoting agents, dispersing agents, preservatives, solubilizing agents, and the like, can be added to a formulation where appropriate.

The compositions of the present invention can include other active agents for treatment of retinal conditions, including, but not limiting to, anti-infective agents, antibiotics, antiviral agents, anti-inflammatory drugs, anti-allergic agents including anti-histamines, vasoconstrictors, vasodilators, local anesthetics, analgesics, intraocular pressure-lowering agents, immunoregulators, anti-oxidants, vitamins and minerals, proteases and peptidases that breakdown endogenous opioids, and the like.

Further disclosed herein are uses of any of the disclosed compositions for the treatment of a condition of the retina. In some examples, the condition of the retina can be selected from glaucoma, macular degeneration, retinitis pigmentosa, diabetic retinopathy and retinal ischemia.

The present disclosure is further illustrated by the following non-limiting examples.

EXAMPLES

Example 1. Materials and Methods

Animals:

Experiments were performed on: (1) wild type (WT) C57BL/6 mice; (2) connexin knockout (KO) mice $Cx36^{-/-}$, $Cx45^{-/-}$, and $Cx36^{-/-}/45^{-/-}$ (double KO) and their heterozygous (Het) littermates; (3) the hereditary glaucoma model DBA/2J mouse strain; and (4) transgenic CB2, Grik4, and Kokcng (Kcng4, Potassium voltage-gated channel subfamily G member 4)-cre lines in which select RGC and (d)AC subtypes express fluorescent markers and can be visualized for histological or electrophysiologic experiments. All strains are currently maintained by our lab in the SUNY College of Optometry animal facility. The Cx36–/– mice and littermates were derived from F2 C57BL/6-129SvEv mixed background litters (Kameritsch P, et al., Cell Death Dis. 4:e584(2013)). The Cx45–/– were generated by crossing Cx45fl/fl mice with mice expressing Cre recombinase under control of the neuron-directed nestin promoter to yield Cx45fl/fl:Nestin-cre mice (Blankenship A G, et al., J Neurosci. 31:9998-10008 (2011); Pang J J, et al., Invest Ophthalmol Vis Sci. 54:5151-5162. (2013)). All experiments were performed in adult mice of either sex.

Retina-Eyecup Preparation.

All animal procedures were in compliance with the NIH Guide for the Care and Use of Laboratory Animals and approved by the Institutional Animal Care and Use Committees at SUNY College of Optometry. Experiments were performed on retinas of wild type (WT), connexin knockout (KO) mice ($Cx36^{-/-}$, $Cx45^{-/-}$, and $Cx36^{-/-}/45^{-/-}$ dKO), and their heterozygous (Het) littermates. The methods used to impale and label neurons have been described previously (Hu et al., J Neurosci 23:6768-2777 (2003); Völgyi et al., Journal of Comparative Neurology 512:664-687 (2009)). Briefly, flattened retina-eyecups were placed in a superfusion chamber, which was mounted on the stage of a BX51WI light microscope (Olympus) within a light-tight Faraday cage. An IR-sensitive CCD camera (Dage) captured the retinal image, which was displayed on a video monitor. The retina-eyecups were superfused with a modified, oxygenated Ames medium maintained at 35° C.

Intracellular Injections.

For intracellular injections, neurons were visualized and impaled with standard, sharp glass microelectrodes filled with cytochrome C (CytC, 10 mg/ml) and Neurobiotin (4%) in 0.1 M Tris buffer. Substances were injected iontophoretically for 15-20 min using a sinusoidal current (3 Hz, 1-5 nA p-p).

Microbead Injection.

Experimental glaucoma in mice is induced by IOP elevation achieved by intracameral injections of 10 μm polystyrene microbeads (Invitrogen) as previously described (Chen H, et al., Invest Ophthalmol Vis Sci. 52:36-44 (2011)). The intracameral injections are made unilaterally with 2 μl of microbead suspension containing ~7.2×106 beads using a glass micropipette attached to a microliter syringe. An equivalent volume of phosphate-buffered saline (PBS) is injected in contralateral eyes to serve as a control. Measurements of IOP are made with the commercially-available Tonolab tonometer (Colonial Medical Supply) and are performed weekly for up to 8 weeks after the microbeads injection. Measurements are made between 10 μM and 12 PM, to minimize the effect of diurnal IOP variations. Six IOP measurements are made at each interval and averaged.

Immunocytochemistry.

After experimental treatment, retinas were fixed with 4% paraformaldehyde in a 0.1 M phosphate buffer solution (PBS; pH 7.4) for 30 minutes at room temperature, cryoprotected in 30% sucrose, embedded in Tissue-Tek OCT Compound (Andwin Scientific) and frozen. Cryosections (18-20 μm thick) were cut and mounted on microscope slides. For immunostaining, sections were blocked in 3% donkey serum in 0.1M PBS supplemented with 0.5% Triton X-100, and 0.1% NaN3 for 1 h at room temperature. Primary antibodies were diluted in 0.1M PBS with 0.5% Triton X-100, 0.1% NaN3 and 1% donkey or goat serum. Tissues were then incubated with primary antibodies for 3 hours at room temperature or overnight at 4° C. The following primary antibodies were used: rabbit anti-calretinin 1:2000, rabbit anti-calbindin 1:1000, goat ant-ChAT 1:100 (all from Millipore), rabbit anti-GFAP 1:1000 (Invitrogen), rabbit anti-active caspase 3 1:200 (Abcam); mouse anti-Cx35/36 1:300, mouse anti-Cx45 1:300 (both from Millipore). After extensive washing with 0.1M PBS, tissues were incubated for 1 hour in secondary anti-goat/rabbit/mouse antibodies conjugated to Alexa-488 or Alexa-594 (1:200, Molecular Probes). Retinal sections were counterstained with the nuclear dye propidium iodide (PI, Molecular Probes). Neurobiotin was visualized with Alexa-488/594 conjugated streptavidin (Molecular Probes, 1:200). Tissues were then flat-mounted in Vectashield media (Vector Labs) and fluorescent images were taken using a fluorescent microscope or an Olympus FV1200 MPE confocal microscope.

Induction of Cell Death.

Various methods were employed to produce cell death. (1) Single cell apoptosis: CytC was injected into individual RGCs or Müller cells for 15 minutes after which retinas were incubated for 4 hours in oxygenated Ames medium before fixation. After streptavidin histology, apoptotic cells were detected with an anti-active caspase 3 antibody or with Terminal deoxynucleotidyl transferase dUTP nick end labeling (TUNEL) staining. (2) Excitotoxicity: To assess the contribution of GJs to cell death within populations of RGCs and amacrine cells we conducted parallel experiments in which retinas were preincubated for 20 minutes in normal Ames medium or in one containing the GJ blockers meclofenamic acid (MFA; 50 µM) or 18-beta-glycyrrhetinic acid (18Beta-GA; 25 µM). Both control and drug-treated retinas were then exposed for 1 hour to NMDA (100-300 µM) to induce excitotoxicity followed by 4 hours in the control Ames solution. (3) Retinal ischemia: Transient in vivo retinal ischemia was induced by introducing into the anterior chamber a 33-gauge needle attached to a saline-filled reservoir (0.9% sodium chloride) that was raised above the animal so as to increase intraocular pressure (IOP) to a level 120 mm Hg above systolic blood pressure. MFA (2 µl, 500 µM) was administered intravitreally either 30 minutes before or 3 and 24 hours following the ischemic insult. The opposite eye was cannulated, but maintained at normal IOP to serve as a normotensive control. After 40-50 minutes, the needle was withdrawn and ischemia was evidenced by corneal whitening. After 7 days of reperfusion, mice were sacrificed and eyes were processed to assess retinal damage and neuronal death. We also employed oxygen-glucose deprivation (OGD) to induce in vitro ischemia, in which retina-eyecups or isolated retinal whole-mounts were exposed continuously to either a control, oxygenated Ringer solution, or one that was glucose-free and deoxygenated by bubbling extensively with 95% $N_2$/5% $CO_2$ at 34° C. Following 60 minutes in the OGD environment, retinas were transferred to a control, oxygenated Ames medium for 4 hours before processing to evaluate cell death.

Retrograde Labeling and Visualization of Coupled Cells.

We used retrograde labeling of RGCs with Neurobiotin to visualize populations of amacrine cells in the inner nuclear layer (INL) to which they were coupled. Globes with attached optic nerves were submersed in oxygenated Ames medium and a drop of Neurobiotin (4% in 0.1 M Tris buffer) was applied to the cut optic nerve for 40 minutes. For retrograde labeling limited to RGCs, Neurobiotin was replaced with Lucifer yellow (LY, 3%). In separate experiments, retrograde labeling was performed in both eyes prior to incubating one eye in Ames medium containing MFA (50 µM for 30 minutes) after which both eyes were exposed to NMDA (300 µM) for 1 hour. Frozen retinal sections (20 µm thick) were cut on a cryostat and processed for assessment of cell death in the inner nuclear layer (INL) and ganglion cell layer (GCL).

Assessment of Cell Injury and Cell Death.

Apoptotic and necrotic cell death were assessed by cell counts following: (1) staining with Live/Death Viability Assay (calcein AM/ethidium homodimer (EthD) (Invitrogen); (2) TUNEL, or, (3) labeling for activated caspase 3. For population studies, dead cells were counted manually within 500×500 µm areas (5 areas per retina) from micrographs of whole-mounts using images acquired by confocal microscope. Nuclear cell counts were made per unit length (500 µm) of frozen retinal cross-sections labeled with propidium iodide (2 µg/ml).

In some experiments, cells counts were limited to retrograde labeled RGCs in the GCL or certain subpopulation of amacrine cells, identified by specific markers, such as calretinin (CR), calbindin (CB) and choline acetyltransferase (ChAT) in the INL. Fluorescence intensity measures were made of glial fibrillary acidic protein (GFAP), which is overexpressed in Müller glial cells following retinal injury. Expression of GFAP and connexins were quantified by analysis of confocal images with Metavue software (Molecular Devices). Average pixel fluorescence intensities were measured by using uniform rectangular areas (3-5 per image) extending either from the GCL to the outer limiting membrane for GFAP or through the IPL for connexins. The intensity values were then averaged for at least 5 images from 3-5 independent experiments and data were normalized to controls.

Microbead-Induced Glaucoma.

Experimental glaucoma was induced by intracameral injections of polystyrene microbeads (Chen H, et al., Invest Ophthalmol Vis Sci. 52:36-44 (2011)) in one eye of wild type (WT) mice, connexin knockout (KO) mice and their heterologous (HET) control littermates, with sham injection of the second eye as control. IOP measurements were performed weekly and animals were sacrificed at 1, 4, or 8 weeks after initial bead injection. To access cell loss, RGCs and coupled ACs were retrogradely labeled with optic nerve injection of Neurobiotin and vertical retinal sections were counterstained with DAPI to determine overall nuclear counts. RGCs were also labeled by Brn3a antibody for identification. In addition to cell counts, overall retinal damage was assessed by GFAP expression. In some experiments gap junctions were blocked with meclofenamic acid (MFA) intravitreal weekly injections or genetically ablated in connexin KO mice ($Cx36^{-/-}$, $Cx45^{-/-}$, and $Cx36^{-/-}$/$Cx45^{-/-}$ mice).

Statistics.

Data are presented as mean±standard mean error. The number of measurements carried out for a given experiment (n) are given as x/y where x is the total number of samples in which the measures were made (e.g., flat mount areas or sectional lengths) and y is number of retinas. For microbead injection experiments, data are presented as mean±SEM per 1.3 mm length of vertical section. Statistical comparisons were assessed using Student's t-test. Values of p≤0.05 are considered statistically significant.

Example 2. Gap Junctions Mediate Secondary Cell Death in the Retina

We initially examined whether GJ-mediated secondary cell death occurred in the retina. In these experiments, we performed intracellular injections of single RGCs with CytC to stimulate apoptosis and Neurobiotin to assess GJ coupling. To determine whether apoptosis in a single cell could spread to neighbors through a mechanism other than GJs, we first examined RGCs that were not tracer coupled to other cells (FIG. 1A). We found that injection of CytC initiated cell death in the injected cell within the experimental timeframe of 3-4 hours, but no other neuron neighbors were lost (FIG. 1B,C). In contrast, injection of CytC into RGCs that were coupled to ganglion and/or amacrine cells resulted in the death of not only the injected cell, but also the coupled neighbors (FIG. 1D-F). These results confirmed that secondary cell death does occur in the retina and is dependent on functional GJs. It is important to note that CytC, at 12,000 Daltons, is far too large a molecule to pass across a GJ, indicating that other toxic molecules must be moving intercellularly to promote cell death in coupled neighbors. We also found that secondary cell death occurred in coupled Müller cells, indicating that this mechanism can result in progressive death of glia in addition to neurons (FIG. 1G-I).

Example 3. Pharmacological Blockage of Gap Junctions Reduces RGC Death Under Excitotoxic or Ischemic Conditions To determine the contribution of secondary cell death to the loss of RGCs produced under different neurodegenerative conditions, we examined the effect of GJ blockade on cell loss in the GCL. In initial experiments, we induced excitotoxic cell death by incubating retina-eyecups in 100-300 µM NMDA (FIG. 2A,C). Cell death counts were then performed in these retinas (n=44/5) and compared to retinas that were incubated in the non-selective GJ blockers 18Beta-GA (25 µM) or MFA (50 µm) prior to exposure to excitotoxic conditions (FIG. 2B,D). We found that prior blockade of GJs with either 18Beta-GA (n=12/3) or MFA (n=42/5) significantly reduced (p<0.001 for both drugs) cell death in the GCL induced by excitotoxicity (FIG. 2E). Overall, NMDA-induced cell death was reduced dramatically in the GCL of mouse retinas pretreated with 18Beta-GA or MFA compared to those treated with NMDA alone. In control experiments, application of 18Beta-GA or MFA alone did not affect cell viability (p>0.1), supporting the notion that the GJ blockers had no spurious toxic effects. In addition, MFA, at the concentrations tested here, shows no inhibitory effect on NMDA receptors in neurons, suggesting that the attenuation of NMDA-induced cell death by GJ blockade was not due to reduced NMDA receptor activity. Overall, the significant protective effects of pharmacological GJ blockade suggest that secondary cell death is responsible for the progressive loss of the vast majority of RGCs under excitotoxic conditions.

In a second phase of experiments, we examined the role of secondary cell death in RGCs loss associated with ischemic conditions of the retina. We assessed retinal damage subsequent to ischemia induced in vivo by raising IOP above normal systolic levels. In control retinas (n=19/5), GFAP expression was confined exclusively to astrocytes in the GCL (FIG. 3A,E). Expression of GFAP in ischemic retinas, however, was significantly upregulated as evidenced by the spread of immunolabeling to Müller cell processes at all retinal layers (p<0.01) (FIG. 3B, E). Ischemia also produced a significant reduction in nuclear counts in the GCL (p<0.01) accompanied by a marked thinning of the retina, particularly the inner layers (FIG. 3A,B,D).

To assess the role of GJ-mediated secondary cell damage in ischemic injury of the retina, eyes were injected intravitreally with MFA either before or after insult. Treatment with MFA prior to ischemic induction preserved retinal thickness, cell counts in the GCL, and GFAP expression to levels seen in control retinas (FIG. 3C,D,E). Moreover, the protective effect of MFA administered 3 and 24 hours after transient ischemia was evidenced by maintenance of normal levels of retinal thickness, GFAP expression, and cell counts in the GCL measured one week after insult; p<0.01 for all measures (FIG. 3C,D,E).

Example 4. Gap Junctions Mediate Amacrine Cell Loss Following Retinal Injury 15 of the 22 morphological subtypes of RGCs in the mouse retina are coupled to amacrine cells. This extensive coupling suggests that the GJ-mediated secondary cell death may also progress from RGCs to coupled amacrine cell neighbors. To test this idea, we examined the loss of amacrine cell populations immunolabeled with calretinin (CR), calbindin (CB) or choline acetyltransferase (ChAT).

Initial experiments were carried out to determine whether CR-, CB-, and ChAT-immunopositive amacrine cells (ACs) were indeed coupled to RGCs. Ganglion cell somata were retrogradely labeled with Neurobiotin through the cut optic nerve. A large number of cells in the INL and GCL were immunoreactive to CR and ChAT with three distinct IPL bands of CR-labeled dendritic processes and two clear ChAT bands of starburst-a and starburst-b ACs (FIG. 4A,C). In addition to CR-positive RGCs (or displaced amacrine cells) in the GCL, we found (n=18/4) that approximately one-half of the CR-positive, presumed ACs in the INL showed Neurobiotin labeling (FIG. 4A, E, G), suggesting that they were coupled to RGCs. Indeed, blockade of GJs with MFA prior to retrograde labeling effectively eliminated all colocalized labeling of CR-positive ACs in the INL with Neurobiotin (n=8/3, p<0.01) (FIG. 4B,E). CB-immunoreactive labeling in the mouse retina is known to mimic labeling for CR, suggesting that they may label the same subpopulations of ACs and RGCs. Our results from CB-immunolabeled retinas were similar to those described for CR.

Although starburst ACs in the rabbit retina are not coupled to RGCs, we found a small number (less than 10%) of ChAT-positive cells in the INL of the mouse retina that were labeled with Neurobiotin (n=16/3) (FIG. 4C, F, G). However, application of MFA did not produce a significant reduction in the number of ChAT-positive ACs labeled with Neurobiotin (n=6/3; p>0.1) (FIG. 4D, F). We conclude that, at best, only a small number of starburst-a ACs are coupled to RGCs.

In the next set of experiments, we examined how AC death due to excitotoxicity was affected by blockade of GJs with MFA. Application of NMDA produced a significant reduction of CR- (n=18/3; p<0.01) and CB-immunopositive (n=22/3; p<0.01) subpopulations of ACs in the INL (FIG. 5A-H). However, blockade of GJs with MFA prevented the loss of CR- (n=10/3) or CB-immunolabeled (n=6/3) ACs (p<0.01), preserving levels seen in control retinas (FIG. 5C, D, G, H). In contrast, NMDA-induced excitoxicity did not produce a significant reduction in the number of ChAT-positive ACs in the INL (n=20/4; p>0.1), nor was this affected by GJ blockade with MFA (n=17/4; p>0.1) (FIG. 5L).

Amacrine cell death following transient ischemia paralleled the results seen following excitotoxic insult. Ischemia produced a significant loss of CR- (n=48/5; p<0.001) and CB-immunoreactive (n=17/3; p<0.001) subpopulations of ACs in the INL and a disorganization of the dendritic bands in the IPL (FIG. 6A-H). Application of MFA prevented the loss of both the CR- (n=26/5; p<0.001) and CB-immunoreactive (n=21/3; p<0.001) ACs, maintaining levels to that seen in control retinas (FIG. 6C, D, G, H). In contrast, induction of ischemia had no statistically significant impact on the number of ChAT-immunopositive amacrine cells in the INL (n=25/4; p>0.1) (FIG. 6L). As expected, treatment of ischemic retinas with MFA had no effect on the number of ChAT-positive ACs in the INL (n=23/4; p>0.1) (FIG. 6K, L).

Example 5. Gap Junctions Mediate Secondary Cell Death in a Connexin-Specific Manner The inner plexiform layer (IPL) of the retina contains an assortment of GJs formed between RGCs, ACs, and bipolar cell axon terminals that express at least three different connexin subunits. This diversity raises the notion that different cohorts of GJs, possibly based on their connexin profiles, may be responsible for secondary cell death in the inner retina arising from different primary insults. Our results using the GJ blockers MFA and 18Beta-GA did not address this issue. To test this idea, we therefore examined the extent of excitotoxic and ischemic cell death in mice in which Cx36 and/or Cx45, the two most highly expressed subtypes in the IPL, were genetically deleted.

We induced excitotoxic cell death as described above by application of NMDA to retinas of $Cx36^{-/-}$, $Cx45^{-/-}$, and $Cx36^{-/-}/Cx45^{-/-}$ dKO mouse retinas and their heterozygous littermates. Detection of dead cells in the GCL showed that NMDA-induced excitotoxic cell death was markedly reduced in Cx36−/− mouse retinas (n=35/3) as compared to levels found in Het littermates (n=35/3) or WT mice (n=14/3; p<0.001 for both) (FIG. 7A, B, E). In contrast, the extent of cell death in the GCL of Cx45−/− mouse retinas following exposure to NMDA was not statistically different from control levels in Het or WT mice (n=17/3; p>0.1) (FIG. 7A, C, E). We next induced excitotoxic cell death in $Cx36^{-/-}/Cx45^{-/-}$ dKO mouse retinas (n=13/3) and found that the level of cell death in the GCL was indistinguishable from those found in NMDA-treated retinas of $Cx36^{-/-}$ mice (p>0.1) (FIG. 7B, D, E). Thus, the degree of cell death was not additive when both Cx36- and Cx45-expressing gap junctions were deleted. Overall, these results indicated that whereas GJs expressing Cx36 played a role in secondary cell death associated with excitotoxicity, those expressing Cx45 made no significant contribution.

In the next phase of experiments, we induced transient retinal ischemia in vivo in $Cx36^{-/-}$ and $Cx45^{-/-}$ mice and their Het littermates. After 7 days of survival, evaluation of retrograde labeling of GCs with Lucifer yellow (LY) in whole mount retinas revealed a significant loss of axonal processes in Cx36−/− and Het mouse retinas as compared to control levels (FIG. 8A-C). In contrast, ischemic retinas from $Cx45^{-/-}$ mice showed axonal labeling that was comparable to that seen in control retinas (FIG. 8A, D). Consistent with these findings, ischemia resulted in a marked reduction of cells in the GCL of $Cx36^{-/-}$ (n=24/4) and Het littermate mouse retinas (n=28/3; p<0.001 for both), but no significant loss in the GCL of $Cx45^{-/-}$ mice (n=74/5), when compared to control levels (n=54/5; p>0.1) (FIG. 8I). The GFAP immunoreactivity was also markedly increased in Müller cell processes following ischemic insult of $Cx36^{-/-}$ (n=24/4) and Het (n=24/4) mouse retinas (p<0.001), but showed levels in $Cx45^{-/-}$ mouse retinas (n=22/4) that were indistinguishable from that measured in control retinas (p>0.1) (FIG. 8E-H, J).

A differential contribution of Cx36- and Cx45-expressing GJs to secondary neuronal death was also observed under condition of oxygen-glucose deprivation (OGD), an in vitro model of ischemia. Exposure to OGD conditions produced a significant loss of neurons in the GCL of $Cx36^{-/-}$(n=12/3) and Het mouse retinas (n=12/3; p<0.001), but produced no significant loss of cells in the GCL of Cx45−/− mouse retinas (n=10/3; p>0.1).

We then investigated any changes in the distribution of Cx36- and Cx45-expressing GJs under excitotoxic and ischemic insult that could instruct their differential roles in secondary cell death (FIG. 9E, F, K, L). Induction of ischemia produced a dramatic reduction in the expression of Cx36 puncta in the IPL (n=7/3), compared to that in control retinas (n=21/3; p<0.001) (FIG. 9A, B). Instead, we found intense Cx36 immunolabeling in RGC somata indicating an accumulation of the protein in the cytoplasm (FIG. 9B, inset). The expression of Cx45 puncta in the IPL was unaffected by ischemic insult (n=26/4; p>0.1) (FIG. 9G, H, J). However, exposure of retinas to NMDA to induce excitotoxicity had no effect on the expression of Cx36 puncta in the IPL (n=8/3; p>0.1), but dramatically reduced the expression of Cx45 (n=8/4), compared to control levels (n=28/4; p<0.001) (FIG. 9I, J). Thus, ischemic and excitotoxic insult had opposite effects on the expression of Cx36- and Cx45-expressing GJs in the inner retina, consistent with their differential roles in mediating secondary cell death under these two pathological conditions (FIG. 9E, F, K, L).

Example 6. Secondary Cell Death Via GJs Plays a Critical Role in the Progressive Loss of RGCs and ACs in Experimental Glaucoma We next studied the role of secondary cell death in the progressive loss of RGCs and ACs in a mouse model of glaucoma and determined whether pharmacologic or genetic blockade of GJs forms a novel approach for protection of neurons in glaucomatous retinas. We posited that GJ-mediated secondary cell death forms a critical mechanism in the loss of retinal neurons seen in glaucoma and thus blockade of GJs could offer a novel strategy for protecting cells.

Experimental glaucoma was induced by intracameral injections of polystyrene microbeads in one eye of wild type (WT) mice, connexin knockout (KO) mice and their heterologous (Het) control littermates, with sham injection of the second eye as control. Injection of polystyrene beads significantly raised IOP from 11.4±0.3 to 21.9±0.5 mm Hg, which remained elevated for at least 8 weeks following injection (FIG. 10A). We found no significant change in the RGC count from control levels (50±1; p>0.1) within 1 week of bead injection. However, there was a significant decrease in RGC count 4 weeks (40±3; p<0.05) and 8 weeks after bead injection (33±1; p<0.001), a 20% and 36% population decrease, respectively (FIG. 10D). Overall retinal injury following bead injection was evidenced by an upregulation of GFAP in Muller cell processes spanning all retinal levels (FIG. 10B-C).

To test the role of secondary cell death via GJs in the loss of RGCs we next blocked GJs before and after bead injection with MFA (50 μM). Blockade of GJs with MFA prevented the loss of RGCs by bead injection as evidenced by cell counts of 47±4 (p>0.1) at 8 weeks, comparable to those in control retinas (FIGS. 11A-11F). Injection of MFA alone in control eyes had no detectable effect on RGC counts. FIGS. 11D-E show histograms comparing the total cell (RGC+dAC) and RGC counts in the GCL of microbead-injected retinas from WT mice untreated (D) or treated with MFA (E) to block GJs. Microbead injection clearly induced cell loss in the GCL, but blockade of GJs prevented the loss. Thus, pharmacological blockade of GJs with MFA promotes RGC protection in experimental glaucoma.

To determine whether the contribution of GJs to RGC death was connexin-specific, we induced experimental glaucoma in connexin KO mice (FIGS. 14A-14E). At 8 weeks after bead injections the RGC count was 40±1 in Cx36 KOs, 43±1 for Cx45 KOs, and 49±3 for Cx36/45 dKO, indicating a 41%, 59%, and 94% increase in survivability, respectively (FIG. 14A). GFAP expression was also significantly reduced in connexin KO mouse indicating an overall reduction in cell death (FIGS. 15A-15E). Since the majority of RGCs subtypes are coupled to (ACs) in the mouse retina, we examined whether RGC could lead to AC death in experimental glaucoma. We observed a 20-30% loss of ACs in bead-injected WT mouse retinas, which was significantly prevented in Cx36 KO mice (FIGS. 12A-12I). Ablation of Cx45 also prevented loss of coupled dACs (FIGS. 13A-13B). Microbead injection resulted in a loss of coupled dACs in wild-type, and a small increase in uncoupled dACs (FIG. 13A). However, there was no loss in coupled or uncoupled dACs in the Cx45−/− mouse retinas (FIG. 13B).

Our results provide clear evidence that GJ-mediated secondary cell death plays a significant role in the propagation of cell loss in the adult retina seen under a number of different primary insult conditions. First, we observed that injection of the apoptotic agent CytC into individual RGCs and glia led to the exclusive loss of neighboring neurons to which they were coupled via GJs. Second, pharmacological blockade of GJs under excitotoxic and ischemic insult increased the survival of RGCs by approximately 70%, indicating that GJ-mediated secondary cell death plays a major role in cell loss. Further, under these same insult conditions, blockade of GJs prevented nearly all AC death presumably by eliminating the propagation of toxic signals from RGCs to which they were coupled. Finally, selective genetic ablation of the GJ subunits Cx36 or Cx45 found in the inner retina resulted in a significant reduction in the loss of RGCs normally seen following excitotoxic or ischemic insult.

Studies of glaucomatous human retinas have reported an apparent delayed or secondary degeneration of amacrine cells subsequent to RGC cell loss. Consistent with this scenario is our present finding that CR- and CB-immunopositive amacrine cell lose due to excitotoxicity or ischemia could be largely blocked by GJ blockade. These data suggest that while RGCs were most vulnerable under our experimental insult conditions, the loss of ACs was consequent to GJ-mediated bystander cell death. This hypothesis is supported by our finding that ChAT-immunopositive ACs, which showed only minimal coupling to RGCs, were not significantly affected by excitotoxic or ischemic insult nor by disruption of GJs. A downregulation of CR, CB, and ChAT have been reported in ischemic retinas; however, we found that ChAT-immunoreactve cells were unaffected under our ischemic conditions and that MFA could maintain cell counts at control levels. These findings argue that the loss of CR and CB immunolabeling in ischemic retinas more likely reflected cell loss associated with GJ-mediated bystander cell death and not a downregulation of the protein markers.

In contrast to a role in secondary cell death, GJs have been reported to sometimes play a neuroprotective role. This raises the possibility that the role played by GJs in subserving cell death or neuroprotection may depend on the nature of the primary insult.

Our results revealed another important difference between GJs in terms of their role in secondary cell death under different insult conditions. We found that whereas genetic ablation of Cx36, but not Cx45, could significantly reduce cell loss under excitotoxic insult, ablation of Cx45, but not Cx36, protected cells from ischemic injury. These data indicate that different cohorts of GJs, dependent on their connexin makeup, subserve the bystander effect under different pathological conditions. Our results are the first to show that different cohorts of GJs, based on the connexin they express, subserve secondary cell death under different primary insult conditions. Our immunolabeling data suggests that this differential contribution of GJs under excitotoxic and ischemic conditions reflects changes in connexin protein expression and manifestation. Under ischemic insult, we found that Cx36 protein was accumulated mainly in a perinuclear region of RGCs, but the normal punctate immunolabeling in the IPL indicative of dendritic GJs was absent. A similar cytoplasmic internalization has been reported for Cx43 in ischemic cardiac tissue, resulting from a dysfunction in Cx43 trafficking linked to altered serine phosphorylation (Smyth et al., Traffic; 15(6):684-99 (2014); Cone et al., J Biol Chem 289:8781-8798 (2014)). Thus, in our experiments, while Cx36 protein was still manufactured under ischemic conditions, it appears to have not been inserted in the membrane as functional GJs. In contrast, Cx45 punctate labeling in the IPL appeared normal. These findings can explain why ischemic cell loss was reduced in the Cx45−/− mouse retina, but not by ablation of Cx36, namely that Cx36-expressing GJs were already disrupted by the insult. In contrast, we found that Cx45 immunolabeling under excitotoxic insult was abnormal, with punctate labeling absent from the IPL, whereas Cx36 expression appeared normal. These data suggest a downregulation of Cx45 under excitotoxicity and a lack of functional GJs they constitute, which can explain why ablating Cx45 did not reduce cell loss after NMDA-induced excitotoxicity.

The finding that bystander cell death in the retina is ultimately responsible for the loss of most retinal neurons reveals that GJs form a novel, important target for neuroprotection. The identification of GJs as a therapeutic target is lent support by our ability to significantly limit neuronal cell loss by blocking GJs with MFA administered after ischemic insult. Moreover, the finding that limited cohorts of GJs, specifically GJs expressing Cx36 and/or Cx45, are responsible for bystander death is propitious, as it shows that targeting of GJs, by inhibition of these specific connexins, has the potential for treating retinal conditions associated with bystander cell death.

What is claimed is:

1. A method of treating glaucoma by blocking gap junctions comprising administering a therapeutically effective amount of a non-selective inhibitor of connexin 36 to a subject in need thereof, wherein said non-selective inhibitor is 18-Beta-glycyrrhetinic acid (18Beta-GA), and wherein the therapeutically effective amount is at a concentration of 25 μM.

2. The method of claim 1, comprising repeat administration of said inhibitor for a period of 1 week to 1 year.

3. The method of claim 1, wherein said administration is topical administration or intraocular injection.

* * * * *

SEQUENCE LISTING

<160> NUMBER OF SEQ ID NOS: 2

<210> SEQ ID NO 1
<211> LENGTH: 1096
<212> TYPE: DNA
<213> ORGANISM: Homo sapiens

<400> SEQUENCE: 1
tcccattctg gaagtgcggc ccggggaggg gccaggagcg ggaacgtgcc cggtgctgcc        60
cagtctttgt ctgctgcctc cggatgcaca gcgatggggg aatggaccat cttggagagg       120
ctgctagaag ccgcggtgca gcagcactcc actatgatcg ggaggatcct gttgactgtg       180
gtggtgatct tccggatcct cattgtggcc attgtggggg agacggtgta cgatgatgag       240

-continued

```
cagaccatgt tgtgtgcaa caccctgcag cccggctgta accaggcctg ctatgaccgc      300
gccttcccca tctcccacat acgttactgg gtcttccaga tcataatggt gtgtaccccc      360
agtctttgct tcatcaccta ctctgtgcac cagtccgcca agcagcgaga acgccgctac      420
tctacagtct tcctagccct ggacagagac ccccctgagt ccataggagg tcctggagga      480
actgggggtg gggcagtgg tgggggcaaa cgagaagata agaagttgca aaatgctatt       540
gtgaatgggg tgctgcagaa cacagagaac accagtaagg agacagagcc agattgttta      600
gaggttaagg agctgactcc acacccatca ggtctacgca ctgcatcaaa atccaagctc      660
agaaggcagg aaggcatctc ccgcttctac attatccaag tggtgttccg aaatgccctg      720
gaaattgggt tcctggttgg ccaatatttt ctctatggct ttagtgtccc agggttgtat      780
gagtgtaacc gctaccccctg catcaaggag gtggaatgtt atgtgtcccg gccaactgag     840
aagactgtct ttctagtgtt catgtttgct gtaagtggca tctgtgttgt gctcaacctg      900
gctgaactca accacctggg atggcgcaag atcaagctgg ctgtgcgagg gctcaggcc      960 aagagaaagt caatctatga gattcgtaac aaggacctgc aagggtcag tgttcccaat      1020 tttggcagga ctcagtccag tgactctgcc tatgtgtgag agggcaggtt tcatgaaggt     1080
ctgggggatg gcaagg                                                     1096
```

<210> SEQ ID NO 2
<211> LENGTH: 7643
<212> TYPE: DNA
<213> ORGANISM: Homo sapiens

<400> SEQUENCE: 2

```
gcagcggcgg gagcggcttc tgcctcggct ggagactgag gcgaaggcgg cagcggcgga       60
ggaggtggag gagaggcgag ggtgaaggcg atggcgacgc ggggcacatg aggccgcgac      120
cggcgggacg ggccgaggcc cggcggagga ggcggctccg ggggaacccg ccgcggagg      180 gaatctggaa aaattgcaat caaaacatca tttctctaag aaaattttgg gtaaccgaag      240
ttctggacaa cagggcatac caattcaatc accatgagtt ggagcttcct gactcgcctg      300
ctagaggaga ttcacaacca ttccacattt gtggggaaga tctggctcac tgttctgatt      360
gtcttccgga tcgtccttac agctgtagga ggagaatcca tctattacga tgagcaaagc      420
aaatttgtgt gcaacacaga acagccgggc tgtgagaatg tctgttatga tgcgtttgca      480
cctctctccc atgtacgctt ctgggtgttc cagatcatcc tggtggcaac tccctctgtg      540
atgtacctgg gctatgctat ccacaagatt gccaaaatgg agcacggtga agcagacaag      600
aaggcagctc ggagcaagcc ctatgcaatg cgctggaaac aacaccgggc tctggaagaa      660
acggaggagg acaacgaaga ggatcctatg atgtatccag agatggagtt agaaagtgat      720
aaggaaaata aagagcagag ccaacccaaa cctaagcatg atggccgacg acggattcgg      780
gaagatgggc tcatgaaaat ctatgtgctg cagttgctgg caaggaccgt gtttgaggtg      840
ggttttctga tagggcagta ttttctgtat ggcttccaag tccacccgtt ttatgtgtgc      900
agcagacttc cttgtcctca taagatagac tgctttattt ctagacccac tgaaaagacc      960
atcttccttc tgataatgta tggtgttaca ggcctttgcc tcttgcttaa catttgggag     1020
atgcttcatt tagggtttgg gaccattcga gactcactaa acagtaaaag gagggaactt     1080
gaggatccgg gtgcttataa ttatcctttc acttggaata caccatctgc tccccctggc     1140
tataacattg ctgtcaaacc agatcaaatc cagtacaccg aactgtccaa tgctaagatc     1200
```

```
gcctacaagc aaaacaaggc caacacagcc caggaacagc agtatggcag ccatgaggag    1260
aacctcccag ctgacctgga ggctctgcag cgggagatca ggatggctca ggaacgcttg    1320
gatctggcag ttcaggccta cagtcaccaa acaaccctc atggtccccg ggagaagaag     1380
gccaaagtgg ggtccaaagc tgggtccaac aaaagcactg ccagtagcaa atcaggggat    1440
gggaagacct ccgtctggat ttaatcctgg cgggcttaaa acctgtgctt ttcatagttt    1500
atggtaagca gcagctcact gaataatgac ttccattgag taaacatttg gctctggtta    1560
tcttcaggga tgctgttggc tcatgatcca agctcagggg actctggagg cggggctggg    1620
ctgagggaga gaaagggaaa cacagtgttc ccaggcacat gttcttagca ataatacagt    1680
tgcagaactt tacatttgtg tcttccagat ctggagaaga acagacatat ttaaatcatt    1740
cttgttgaac agttttgta tgtacagtat tatggtactt ttttttttt agtatgagaa       1800
cttttttgt atttgtacat tgaactgctg tagttatact tttatattaa aggggaaaaa     1860
gtccttataa ataatgccta ttaggctagt gctattactt tgttcagcaa attctaccct    1920
ggctttagag tttttaatag atgctacacc taataaaagt gcctctcata ttgcaggaac   1980
gatttcagat gtgtaaggag actgaagagg agataccagt ttttagtctt ggaaagcaag    2040
ttcacagtag aaggaggttg agatctttct tttatgtgag aaatctttga atctcattca    2100
tgcgatcaga gttgtagcca attttttgaaa accttatttt caaggaaat aaatgattca    2160
ctgtaggatt cctttaaata tcaagcatca ccagtatatg ctttgatggt atatgtatat   2220
aacttaaagt tctttcaaaa gcctgataca gaaacgtgtc cccagtttgg tagcaatgtg   2280
gaaaacctgg ctagagatga tatggagctg tccctcagaa agcaaagcca tgcctggaat   2340
ccctaatagg ctgcttagtt gtgaacctgt ttgatttgcc ttaagcctct atccagaaac   2400
ctgcccgctt ccgtctggtt aagaagccag tggtggatat tttctttgtt aacattagaa   2460
atgcaaacat tcccttgtca accaagaata ctcaaagcta cttgtattgg aaatggcaga   2520
aggcctaaat ccaaatttct tattttttat aatttaccat agaagttttg tgattaaatt   2580
cttacttctg ccagtggagg tttatgcctg aaaggtcatg gggtcctgtc tgtaaataga   2640
cctaaagaga agtgcagtat ttattctttg taggcataat gtgtttgtca ctgacaagca   2700
ttcatgttca tcccactagt cttttattgc agtcttttat tgtcattttc agccttatgt   2760
tggagagctt tgcttctca tcatgttcac attgtcttaa gttttgtgag cttctgagaa     2820
agagcttggt aaaggtttaa aggggacttt gttccaccag ggagcatttt atttgggcgt    2880
ctcacccttt tctaatgaaa gctgttgtaa gccacctctg acttggaaat tctgaaagta   2940
tgaatatttt ttatatctta attgtaaaat gccagttctc cattatttag atgaatagta   3000
gaacactgca ccctttgtgc agtgttttg tttctctact gcattcctac ccccaccaaa    3060
aaaaagaaac ttaaggaaat ttttttttga dacagggtct ccctctttca cccaggctgg   3120
agtgcagcag catgatctca gctcactgca gcctctgcct cccaggctca agcaatcatt    3180
ccacctcagc ctcttgatta gctgggacta caggcatgtg ccaccatact cggctaattc    3240
tgttttaaaa attttttttg tagagatgag gtctcactat gttacccagg ctggtctcga   3300
acttttgggt tcaagtgatc ctcccgcctc agcctctcaa agtgttagta ttataggtgt    3360
gagccaccat gcccagccta gaaaatttaa ccttatcttt tagccattca tttacttta     3420
tttgcttttt taaaaaaaaa tctttaaatt ttagcctaga gaagcacctc aggaactcta   3480
aacatcttag gcaaaaatta aactcaggtg agactgaagg agaaatttca gaaatacaca    3540
tgtacctcat gggtaattaa tagacatgca cagtttcctt caaatcaaat gtttaataag   3600
```

```
gaaattcata taattccaag aaaacaggca aaatttggaa tacataagcc tagctaagat    3660
aaagaactac cagttaattc ttaacatcac tggagcttcc agcaggtttt ttaattgaag    3720
gacaaaaagt gtccatacat ttgtgttatc tcttcagagc ctgagggaga agagagtggc    3780
tttgcccagt ggaaaggctg gggatttgag aatgatacag ggggaaggag tcaagcagaa    3840
atgccaggaa gaaccaggca aagacatttg gcgccagaag catccactta atttctgtga    3900
agagtgcccc tggtgtttca tcttggcctg ttttgatgag aatgttatct tttgtgtctg    3960
gataacgcgt cagcttctta aagtacatat aaagatattc tgtcacctcc ccacatgcac    4020
acacttttaa aatctatttt tattctcttg ctaaagttgt aattatgtca agaattttcc    4080
agctctaact gccttcttag tacatgtctt tctgcctttg aagcatatga gtttgccaaa    4140
gtcattctcc cctaatgaca tattgtggac ttacattaag aaaatgggcc aggcgcggtg    4200
gctcacacct gtaatcccag cactttagga ggcccaggcg ggtggattac ctgaggtcag    4260
gagttcaaga ccagactggt caacatggtg aaactccatc tctactaaaa atacagaaat    4320
tagccaggag tgctgggtgg acgcctgcaa tcccagctac ttgggaggtt gaggcaggag    4380
aattgcttga acccaggagg cagaggttgc agtgagctga gatcatacca ttgcactcca    4440
gcctgcaaga cagagtgaaa ctcttgtctc aaaaaaaaaa aaagaaaaaa agaaagtgag    4500
cctgttgatg tctagctaac ccattggtgg agtctgcatt gaatctgtaa gaatattgtt    4560
ctggatcatg caggtgggat ttgtataaaa agcctgtcca acatttagtt ctcactcgca    4620
tcagaatcat actgttttga attgccatat aagacatgct ccatcatgac acttgcttct    4680
cctccaaata caagttgagt gcttagtcct tcacctgcta gaatcaggat acaatcaaca    4740
tgattatgtt ccttaacaca cttggattta tgcagatgtg gtgtgtcctt tgctctttt     4800 tttcttaaga cagagtcttg ctcttgtcgc tcaggctgga gtgcagtggt gtgatttcgg    4860
ctcactgcaa cctccgcctc ctgggttcaa gcgattctcc tgcctcagcc tcccgagtag    4920
ctgggattac aggcaccacc accataccag gctgattttt tttgtatttt taatatagac    4980
agggcttcat catgttggcc aggctggcag gctggtctcg aactcctcac ctcgtgatcc    5040
gcccacctca gcttcccaaa gtgctgtgat tacaggcgtg agccaccgcg cctggcctgc    5100
tcttaaaacc cgttattcag aagatttgta aaagaaatag gctttttttt tttttttggt    5160
taattcaaac gaggggaaaa ttagatagca ttttcccta aagaaatgtt aatgttcatt     5220
ttgtggcttt gttttcaagt tcaggagcc atgtacatct cagaagtgtt acgaagtgat     5280
tagaaaaggc ctctggtaaa agaccttcaa ggaccaacca ttattattgg tcacttgttt    5340
gaacttggcg cttaaaaaaa aagttggact gtgatgcttt ggtgctcttt atcacagaca    5400
tcagtgatgg tctgaaacac tctctagcag tttatacgaa gaatggactt acatgttatc    5460
agttacactc atgatttact cgttcagctt ctacaagtcc atactttatg ctgtctcatt    5520
taagagacag tccacttctg aaaataaaat cgatagttga tgatacattt ttggctagcc    5580
agctttctgt aaaaggcaag tatgttagac atgcacagtt tccttcaaat caaatgttta    5640
ataaggtact tcaagaaacg cctttttaaa aatcaaaggt tttggccagg catggtggct    5700
cacgcctgta atcccagcac tttgggaggc caaggtgggc gaatcacaag gtcaggagtt    5760
tgagaccagc ctggccaaca tggtgaaacc ccgtctctac taaaaatacc aaaaattagc    5820
cgggcgtggt ggtgggtacc tgtaatccca gctactcagg aggctgagat gagaatcact    5880
tgatcccagg aggtagaggt tgcagtgagc cgagattgcg ccattgcact tcagcctggg    5940
```

```
caacgagtga aactctcaaa aaaaaattca tagtaataat aaagtccctg catgcagttt    6000
ggaaataaaa tttaaactca tttatgtgta ataaatatgt aataattcac agtcaccatc    6060
aaatgttgga atcattgaat tgcatacttg tactcattcc ggccacatca tgaagtgttt    6120
aaagatttgt atttgctgtt gtccctatgt agttctattg atgtttggtt ttgttttttg    6180
gggtttgttt tgagcccagg ctagagtgca atggcacaat ctcaactcac tacagcctgg    6240
acctccttgg ctcaagcagt cctcccactt cagcctccca agtagctggt ctgcaagtgc    6300
tcaccaccac acctggctaa tttttgtatt ttttgtagag acagagctct cactatgttg    6360
cctagactgg tctcaaactc ctgggcccaa gcaatcctcc catcacagcc tccgaaggtg    6420
ctgggattac aggcataagc cactgtgccc agcctgtttt taataatgat attaagtggg    6480
tttggttcat gtgttattaa tcagtgttaa taatcgtact tttttttttt tttaaaagaa    6540
accatggtat tctaaaatca ggagtccaaa taaaagaaag ttctcggctg tgcatggtgg    6600
ctaacacctg taatcccagc actttgggag gctgaggtgg gtggatcact agaggtcagg    6660
agtttgaaac aagcctggcc aacatggtaa acccccctct ctactaaaaa tacaaaaatt    6720
agccgggcat ggtggtgcac acctgtaatc ccagctactc gggatgttga ggcatgagat    6780
ttccttgaac ctggaaggca gaggttgctg tgagccgaga tcgcgccact gcactccagc    6840
ctgggtgaca gagtaagact gtcgccaaaa aagaggaaaa aagttatcca gtgcagtttc    6900
tacagagata aagaagtaa tagttctggc tgggtgtggt ggcttatgcc tgtaatccca    6960
acactttggg aggccaaggc aggtggatca catgaggtca ggagttcgag accagcctgg    7020
ccaacatggc aaaactgtct ctactaaaaa tataaaaatt aggtatggtg gcacgtgcct    7080
gtacttacag ctacttggga ggctgaggca tgagatgaca atctcttgaa cccaggaggc    7140
ggaggttgca gtgagctgag attgcaccac tgcactccag cttgggtgat ggagtgagac    7200
tcaaataaaa aaggtactag ttctgcattt cagagttggc ttgttgaacc aggctatatg    7260
cttccaagat ttaaatgttt ttctgtatta tactctcaat tgtgttttaa aaaaatctct    7320
tacagaaatc tctacctcag gcactaagtg ttatgacatg ggtagcatat tgatattgaa    7380
aacttagcta ggacttccag ccttttaaga taatttaaat gtaaaattaa atggttaacc    7440
agcaatctaa tgtcatgtgg tgtgcagttt ggatattgca tgaacagcta aggaatcacc    7500
tgttctagtg ccaaagatca ctcattgcta attttgttct gtacagctta tgtaatatt     7560 tcatggtgga gacggactct gtgtgctcag ggccttgtct ctaggaagat tttgtcaatt    7620
ccaaatacag ttttgaagat tca                                            7643
```